US010624663B1

United States Patent
Barral et al.

(10) Patent No.: US 10,624,663 B1
(45) Date of Patent: Apr. 21, 2020

(54) CONTROLLED DISSECTION OF BIOLOGICAL TISSUE

(71) Applicant: Verily Life Sciences LLC, Mountain View, CA (US)

(72) Inventors: Joëlle Karine Barral, Mountain View, CA (US); Benjamin Kreil Yaffe, Mountain View, CA (US); Eden Rephaeli, Menlo Park, CA (US); Chia-Jean Wang, Palo Alto, CA (US); Blake Hannaford, Seattle, WA (US)

(73) Assignee: Verily Life Sciences LLC, Mountain View, CA (US)

( * ) Notice: Subject to any disclaimer, the term of this patent is extended or adjusted under 35 U.S.C. 154(b) by 217 days.

(21) Appl. No.: 15/802,058

(22) Filed: Nov. 2, 2017

Related U.S. Application Data

(62) Division of application No. 14/506,400, filed on Oct. 3, 2014, now Pat. No. 9,833,254.

(51) Int. Cl.
*A61B 17/32* (2006.01)
*A61B 34/20* (2016.01)
*A61B 34/30* (2016.01)
*A61B 17/02* (2006.01)
*A61B 17/3211* (2006.01)
*A61B 18/12* (2006.01)
*A61B 18/20* (2006.01)
(Continued)

(52) U.S. Cl.
CPC .............. *A61B 17/32* (2013.01); *A61B 17/02* (2013.01); *A61B 17/3211* (2013.01); *A61B 18/12* (2013.01); *A61B 18/20* (2013.01); *A61B 34/10* (2016.02); *A61B 34/20* (2016.02); *A61B 34/30* (2016.02); *A61B 1/00009* (2013.01); *A61B 2017/00353* (2013.01); *A61B 2018/00577* (2013.01); *A61B 2018/00601* (2013.01); *A61B 2034/107* (2016.02); *A61B 2034/108* (2016.02); *G16H 50/50* (2018.01); *Y10S 901/41* (2013.01)

(58) Field of Classification Search
CPC .......... A61B 17/32; A61B 34/20; A61B 18/20
See application file for complete search history.

(56) References Cited

U.S. PATENT DOCUMENTS 8,781,630 B2   7/2014   Banks et al.
8,792,963 B2   7/2014   Zhao et al.
(Continued)

OTHER PUBLICATIONS

Leonard, Simon, et al., "Smart Tissue Anastomosis Robot (STAR): Accuracy Evaluation for Supervisory Suturing Using Near-Infrared Fluorescent Markers," IEEE International Conference on Robotics and Automation (ICRA), pp. 1889-1894, 2014.
(Continued)

*Primary Examiner* — Richard G Louis
(74) *Attorney, Agent, or Firm* — McDonnell Boehnen Hulbert & Berghoff LLP

(57) ABSTRACT

A robotic surgical system includes a surgical instrument configured to cut biological tissues and an imaging system configured to image the biological tissues. Based on one or more images of the biological tissue generated by the imager, the robotic surgical system operates the surgical instrument to cut the biological tissue according to a desired dissection of the tissue. The robotic surgical system operates the surgical instrument to partially or wholly automatically perform one or more cuts into the biological tissue to achieve the desired dissection.

12 Claims, 10 Drawing Sheets

(51) Int. Cl.
*A61B 34/10* (2016.01)
*G16H 50/50* (2018.01)
*A61B 18/00* (2006.01)
*A61B 17/00* (2006.01)
*A61B 1/00* (2006.01)

(56) References Cited

U.S. PATENT DOCUMENTS

| | | |
|---|---|---|
| 8,801,661 B2 | 8/2014 | Moll et al. |
| 8,808,164 B2 | 8/2014 | Hoffman et al. |
| 8,810,631 B2 | 8/2014 | Scott et al. |
| 9,833,254 B1 | 12/2017 | Barral et al. |
| 2004/0024311 A1* | 2/2004 | Quaid, III .......... A61B 17/3403 600/428 |
| 2005/0033160 A1* | 2/2005 | Yamagata ................ A61B 6/12 600/425 |
| 2006/0020279 A1* | 1/2006 | Chauhan ................ A61B 90/36 606/167 |
| 2007/0213586 A1 | 9/2007 | Hirose et al. |
| 2008/0103390 A1* | 5/2008 | Contag .............. G01N 21/6428 600/427 |
| 2010/0262162 A1 | 10/2010 | Omori |
| 2011/0319941 A1 | 12/2011 | Bar et al. |
| 2014/0005684 A1 | 1/2014 | Kim et al. |
| 2014/0188132 A1 | 7/2014 | Kang |
| 2016/0030134 A1* | 2/2016 | Shapter ................ G06F 3/0488 606/130 |

OTHER PUBLICATIONS

University of Maryland, A. James Clark School of Engineering, "New Probe Could Help Surgeons Avoid Blood Vessel Damage," News Story, Jan. 23, 2012, http://www.bioe.umd.edu/news/news_story.php?id=6237.

* cited by examiner

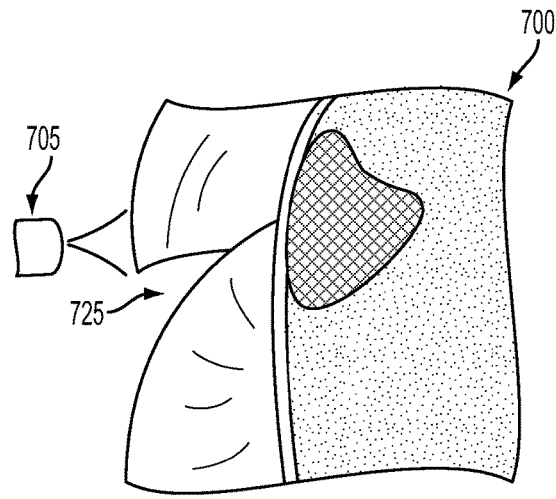
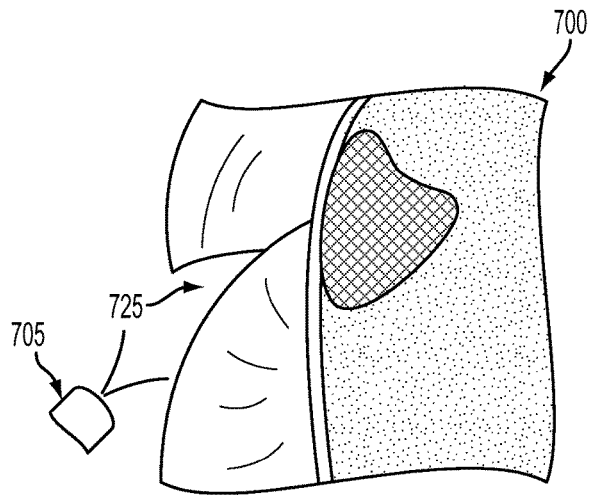
FIG. 7A    FIG. 7B
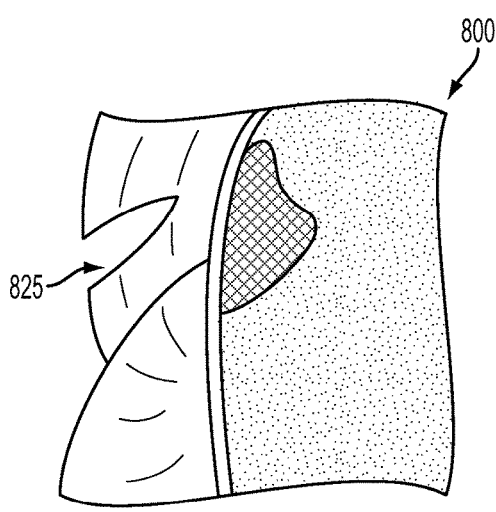
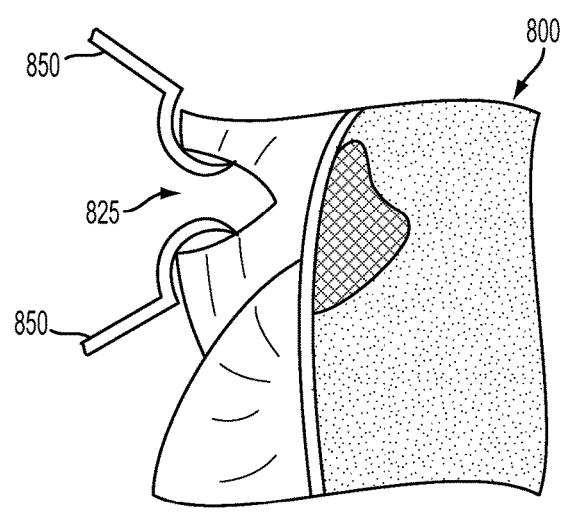
FIG. 8A    FIG. 8B

CONTROLLED DISSECTION OF BIOLOGICAL TISSUE

CROSS-REFERENCE TO RELATED APPLICATION

This application is a division of U.S. patent application Ser. No. 14/506,400, filed Oct. 3, 2014, which is incorporated herein by reference.

BACKGROUND

Unless otherwise indicated herein, the materials described in this section are not prior art to the claims in this application and are not admitted to be prior art by inclusion in this section A variety of robotic systems exist to enable surgical procedures to be performed by a surgeon operating such a robotic system. The surgeon could be proximate to the robotic system (e.g., in the same room as the robotic system and patient, or in an adjacent room) or could be very distant from the robotic system. The commands of the surgeon can be transmitted across the distance (e.g., over the internet) to control the operation of the robotic system; conversely, information generated by sensors of the robotic system (e.g., images generated by cameras, forces detected through surgical instruments) could be transmitted across the distance and presented to the surgeon (e.g., through a display, through haptic feedback). Such robotic systems could include a variety of surgical instruments, including imaging tools, forceps, hemostats, retractors, sources of suction, and scalpels. Further, such robotic systems could include a plurality of actuated robotic arms on which such surgical instruments could be disposed and whose configuration could be controlled directly by a surgeon (e.g., by operating a haptic controller, joystick, or other input(s)). Such robotic systems can enable a single surgeon to perform surgical procedures on patients distributed across a wide geographical region and/or patients located in hard-to-reach locations. Further, such robotic systems can enable a surgeon to have much finer or otherwise improved control of surgical instruments used during a surgical procedure.

SUMMARY

Some embodiments of the present disclosure provide a method including: (i) receiving, by a controller, information indicative of a desired dissection of a biological tissue, wherein the controller is configured to control a surgical instrument, wherein the surgical instrument is configured to cut the biological tissue; (ii) receiving, by the controller, an initial image of the biological tissue; (iii) determining, by the controller, based on the initial image and the information indicative of the desired dissection, an initial trajectory of the surgical instrument to cut the biological tissue; (iv) controlling, by the controller, the surgical instrument based on the initial trajectory, such that the surgical instrument makes an initial cut into the biological tissue; (v) after the surgical instrument has made the initial cut into the biological tissue, receiving, by the controller, a subsequent image of the biological tissue, wherein the subsequent image shows the initial cut and at least a portion of the biological tissue surrounding the initial cut; (vi) determining, by the controller, based on the subsequent image and the information indicative of the desired dissection, whether the initial cut has achieved the desired dissection; and (vii) responsive to determining that the initial cut has not achieved the desired dissection, the controller (a) determining one or more subsequent trajectories of the surgical instrument to cut into the biological tissue, and (b) controlling the surgical instrument based on the one or more subsequent trajectories, such that the surgical instrument makes one or more subsequent cuts into the biological tissue.

Some embodiments of the present disclosure provide a system including: (i) a camera configured to image a biological tissue; (ii) a surgical instrument configured to cut the biological tissue; and (iii) a controller operably coupled to the camera and the surgical instrument, wherein the controller comprises a computing device programmed to perform operations including: (a) receiving information indicative of a desired dissection of the biological tissue; (b) imaging the biological tissue, using the camera, to generate an initial image of the biological tissue; (c) determining, based on the initial image and the desired dissection, an initial trajectory of the surgical instrument to cut the biological tissue; (d) controlling the surgical instrument based on the initial trajectory such that the surgical instrument makes an initial cut into the biological tissue; (e) after the surgical instrument has made the initial cut into the biological tissue, imaging the biological tissue, using the camera, to generate a subsequent image of the biological tissue, wherein the subsequent image shows the initial cut and at least a portion of the biological tissue surrounding the initial cut; (f) determining, based on the subsequent image and the desired dissection, whether the initial cut has achieved the desired dissection; and (g) responsive to determining that the initial cut has not achieved the desired dissection, (1) determining one or more subsequent trajectories of the surgical instrument to cut into the biological tissue, and (2) controlling the surgical instrument based on the one or more subsequent trajectories, such that the surgical instrument makes one or more subsequent cuts into the biological tissue.

Some embodiments of the present disclosure provide a system including: (i) means for imaging a biological tissue; (ii) means for cutting the biological tissue, wherein the means include at least one surgical instrument; and (iii) means for controlling the imaging means and the cutting means and configured to perform operations including: (a) receiving information indicative of a desired dissection of the biological tissue; (b) imaging the biological tissue, using the imaging means, to generate an initial image of the biological tissue; (c) determining, based on the initial image and the desired dissection, an initial trajectory of the surgical instrument to cut the biological tissue; (d) controlling the cutting means based on the initial trajectory such that the cutting means make an initial cut into the biological tissue; (e) after the cutting means have made the initial cut into the biological tissue, imaging the biological tissue, using the imaging means, to generate a subsequent image of the biological tissue, wherein the subsequent image shows the initial cut and at least a portion of the biological tissue surrounding the initial cut; (f) determining, based on the subsequent image and the desired dissection, whether the initial cut has achieved the desired dissection; and (g) responsive to determining that the initial cut has not achieved the desired dissection, (1) determining one or more subsequent trajectories of the cutting means to cut into the biological tissue, and (2) controlling the cutting means based on the one or more subsequent trajectories, such that the cutting means make one or more subsequent cuts into the biological tissue.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7A illustrates a cross-sectional view of an example biological tissue that has been cut in a surgical environment and an imager configured to image the biological tissue.

FIG. 7B illustrates the biological tissue and imager of FIG. 7A after relocation of the imager.

FIG. 8A illustrates a cross-sectional view of an example biological tissue that has been cut in a surgical environment.

FIG. 8B illustrates the biological tissue of FIG. 8A after retraction of tissue on opposite side of the cut by a retractor.

DETAILED DESCRIPTION

Figure 1A:
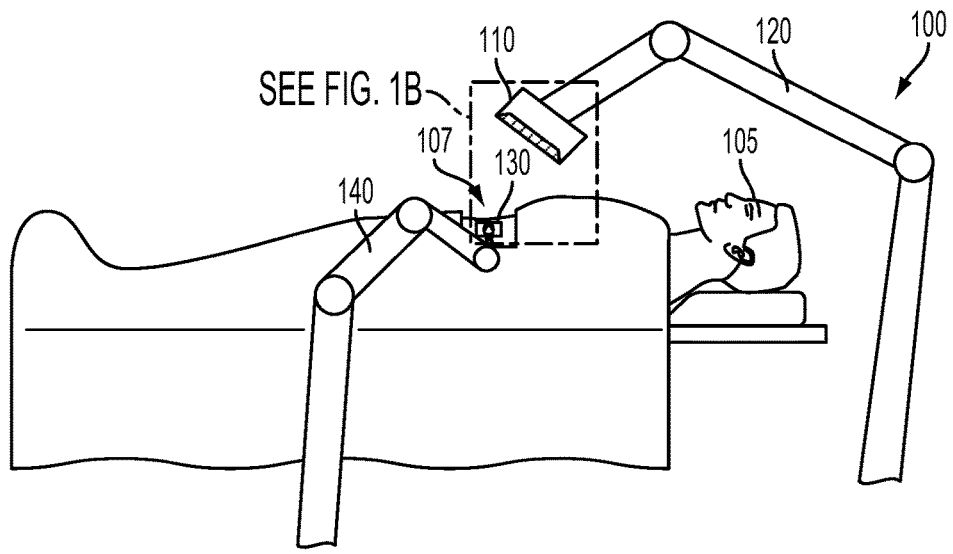
FIG. 1A illustrates an example surgical environment and an example robotic surgical system.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body and/or tissues thereof, it is contemplated that the disclosed methods, systems and devices may be used in any environment wherein partially or wholly automated dissection and/or incision of tissues of an environment is desired. The environment may be any living or non-living human or animal body or a portion thereof, an implanted material, an implantable device, etc. Moreover, while the present disclosure describes embodiments for use in vivo, one of skill in the art will also recognize that in vitro applications are possible as well. Accordingly, the environment may also include a transplant tissue, a cadaver, and/or a stereotaxically or otherwise immobilized tissue.

I. OVERVIEW

A robotic surgical system could be configured to automatically dissect tissues of a human or animal body or to perform some other interaction(s) with the tissues with no or minimal input from a human surgeon. This could include the robotic surgical system imaging the tissues and performing one or more surgical interventions based on resulting images of the tissues, e.g., updating the location or shape of a desired dissection or cut of the tissue based on a detected deformation of the tissue (e.g., due to retraction, movement of a body containing the tissue, or some other cause). The robotic surgical system could be configured to perform a desired dissection (or cut) of tissue to expose an underlying tissue or according to some other application. Specification of a desired dissection of the tissue could be performed by a human (e.g., specified by a surgeon relative to pre-surgical and/or intra-surgical images of the tissue) and/or by a controller (e.g., to expose a target while minimizing trauma applied to the tissues to be dissected). Operation of such a robotic system could rely on regular user input (e.g., user approval of each prospective cut to be performed by the system) or user input in response to a determination of the system (e.g., user approval of a prospective cut to be performed by the system when the system has determined that a blood vessel or other target is proximate to the prospective cut).

A desired dissection of biological tissue could be described relative to one or more images of the biological tissue. In some examples, a desired dissection could be described by the location and shape of a line, plane, two-dimensional surface, or other manifold within the space of an image of the tissue. For example, a desired dissection could be described by a surface described within and relative to a three-dimensional scan (e.g., a CT scan, an MM) of the biological tissue. Information indicative of a desired dissection could be specified by a human (e.g., by a surgeon) and/or determined by a controller of a robotic surgical system or by some other computer. For example, a robotic surgical system could determine a dissection of a biological tissue (using, e.g., MM or other imaging information about the tissue) to expose a target tissue (e.g., a tumor or other region containing tumor cells, a cyst, a foreign body) while minimizing trauma to surrounding tissues (e.g., by specifying the desired dissection to follow a surgical plane between regions of tissue, by minimizing an area and/or volume of tissue proximate to the desired dissection, by specifying the desired dissection to avoid certain tissue, e.g., nerves, blood vessels, tendons). Additionally or alternatively, a desired dissection could be specified in whole or in part by a human (e.g., a surgeon). Information indicative of a desired dissection of tissue could include additional information, e.g., could describe tissues to be avoided when dissecting or otherwise interacting with the tissue (e.g., blood vessels, nerves).

Such a robotic surgical system could be operated in a variety of ways to dissect a biological tissue based on an information indicative of a desired dissection and one or more images of the biological tissue. Generally, such a system could obtain an image of the biological tissue (e.g., by receiving the image from a separate system, or by operating a camera, scanner, or other imager of the system) and could determine an initial trajectory of a cut to wholly or partially implement the desired dissection. This could include registering a pre-surgical image of the biological tissue (relative to which a desired dissection could be specified or indicated) to an initial image of the biological tissue obtained temporally proximate to the performance of actions (e.g., incisions, ablations, or other cutting actions) to implement the desired dissection of the tissue.

Determining an initial trajectory of a cut to wholly or partially implement the desired dissection could include determining an intersection between an exposed surface of the biological tissue (e.g., an external skin surface, an external surface of a subcutaneous tissue that has been exposed by previous dissection and/or retraction) and the location and/or shape of the desired dissection relative to the biological tissue and/or features of the biological tissue (e.g., locations of vessels and/or tissue edges or other features, locations of fiducial markers implanted and/or placed on/within the tissue). The robotic system could then operate a surgical instrument to execute the initial trajectory (i.e., to dissect the tissue according to the initial trajectory). The robotic surgical system could subsequently image the biological tissue to determine a degree to which the operation of the surgical instrument has achieved the desired dissection, and could responsively determine subsequent actions to perform (e.g., subsequent cut trajectories to achieve the desired dissection, update of the desired dissection and/or trajectories determined therefrom, retraction of tissues to expose tissues for further dissection, ablation or other operations relative to an exposed target tissue).

A robotic surgical system as described herein could include a variety of surgical instruments configured to incise, ablate, cauterize, cut, or otherwise dissect biological tissues. Such instruments could be disposed on robotic armatures configured to position the surgical instrument(s) relative to a biological tissue and/or to translate the surgical instrument(s) to dissect the biological tissue and/or to enable other applications of the surgical instrument(s). Instruments or other elements of a robotic surgical system as described herein (e.g., cameras, imagers, retractors) could be configured for use as part of endoscopic surgical interventions, i.e., to image, dissect, cut, ablate, retract, or otherwise interact with biological tissue within a body cavity through one or more holes in the body cavity. In some examples, the surgical instruments could include a surgical laser configured to dissect tissue by ablating the tissue by applying a beam of illumination to regions of the tissue. For example, the surgical laser could be a 2 micron laser, $CO_2$ laser, an excimer laser, or some other variety of laser configured to apply energy to biological tissue sufficient to ablate or otherwise modify the biological tissue. Operation of such a laser to cut along a specified trajectory could include operating optics coupled to the laser to control a direction and/or focus of the beam of illumination emitted by the laser and/or operating an armature on which the laser is disposed to control the location and/or orientation of the laser. In some examples, the surgical instrument could include a scalpel, an ultrasonic scalpel, or some other implement configured to dissect tissue by direct mechanical contact between the biological tissue and one or more cutting surfaces of the surgical instrument. Operation of such a surgical instrument to cut along a specified trajectory could include operating an armature on which the surgical instrument is disposed to control the location and/or orientation of a cutting surface of the surgical instrument along the specified trajectory. Additional and/or alternative cutting surgical instruments (e.g., direct and/or alternating current monopolar and/or mulitipolar electro-cauterizing, electro-ablating, and/or electro-surgical instruments, cryosurgical instruments) are anticipated as part of a robotic surgical system as described herein.

A robotic surgical system as described herein could include and/or be in communication with a variety of imaging systems configured to provide images and other information about a biological tissue, for example to enable image-guided automatic dissection or other surgical manipulations of the biological tissue. Such a system could include one or more cameras configured to generate two-dimensional images of biological tissues. Such images could be color images, black-and-white images, infrared images, ultraviolet images, hyperspectral images, or some other variety of images. In some examples, an imaging system could include a light source configured to illuminate the biological tissue with light at one or more wavelengths. For example, a light source of the imaging system could be configured to emit light at a wavelength corresponding to an excitation wavelength of a fluorophore present in the tissue, and a camera or other light-sensitive element of the imager could be configured to detect light emitted by the fluorophore in response to illumination (e.g., to detect light at an emission wavelength of the fluorophore). The fluorophore could be configured to selectively interact with an analyte and/or tissue of interest (e.g., to selectively bind to cancer cells) such that imaging the fluorophore could enable imaging of the target in the biological tissue. A camera or other elements of such an imaging system could be disposed on a robotic armature configured to position the camera or other elements relative to the biological tissue, e.g., to enable regions of the biological tissue (e.g., regions at the base of a cut or other dissection in the tissue) to be imaged despite occlusion by the biological tissue. An imaging system could include ultrasonic imagers, 3D scanners (e.g., scanning lasers and light sensors configured to enable the mapping of a surface of the biological surface), CT scanners, magnetic resonance imagers, or some other variety of imagers and/or combination of imaging technologies.

A robotic surgical system as described herein could include further surgical instruments or other elements configured to image, manipulate, apply suction to, apply saline or other fluids to, cut, cool, heat, deform, clean (e.g., by removing detritus, fragments of suture or other foreign bodies, fragments of resected tissue), manipulate, or otherwise interact with biological tissues. Such elements of the robotic surgical system could be disposed on robotic armatures configured to position the elements relative to a biological tissue and/or to effect some application(s) of the elements. In some examples, the elements could include a retractor configured to apply separating forces between two or more portions of tissue. Such a retractor could apply separating forces through suction, adhesion (e.g., by a liquid and/or dry adhesive), smooth surfaces, gripping surfaces, penetrating prongs, or some other mechanical elements. For example, a retractor could include two self-retaining blades (e.g., mechanical elements having sharp and/or blunted prongs configured to secure a biological tissue) connected to an actuator (e.g., a servo, a motor) configured to apply a separating force force) between the blades.

Applying a separating force could include applying opposing forces to two or more portions of tissue opposite a cut (or other hiatus or interruption in tissue) such that a magnitude of the separating force and/or a displacement between the blades is controlled. A magnitude of a separating force and/or a displacement between the blades could be controlled to stay at a constant level over time (e.g., a fixed magnitude and/or displacement), could be controlled to have a linearly increasing value over time, or according to some other time-dependent pattern. Such a retractor could be configured to separate two portions of tissue opposite a dissection in the biological tissue (e.g., opposite a cut created by the robotic surgical system). Such separation could allow further dissection of tissue according to a previously specified desired dissection or could manipulate tissue to enable dissection according to an updated and/or newly determined desired dissection. Manipulation of tissue by the retractor could additionally allow for imaging of tissues at the base and/or along the walls of a dissection or at some other location(s) that are occluded from the view of one or more imagers by other tissues and/or surgical instruments. Additional and/or alternative surgical instruments or other elements of a robotic surgical system as described herein are anticipated.

Other configurations, modes and methods of operation, and other embodiments are anticipated. Systems and/or methods described herein could include additional imaging modalities, cutting methods or mechanisms, retraction means and mechanisms, or other surgical instruments or other elements to provide additional information about tissues or other contents of a surgical field and/or to provide additional means of resecting, dissecting, ablating, or otherwise modifying tissues according to an application. A system as described herein could include multiple scanners, multiple cameras or other light sensors, multiple cutting means or other surgical instruments (e.g., multiple surgical lasers, actuated scalpels, actuated ultrasonic scalpels, and/or), multiple actuated retractors, and/or additional components according to an application. Systems as described herein could be applied toward implementing, planning, and/or assessing a surgical intervention (e.g., exposing, ablating, resecting, and/or assessing a tissue, recording information related to such operations), imaging a tissue, biopsying a tissue, or some other application. In some examples, a robotic surgical system could be configured to operate automatically (e.g., to cut tissue according to a cut geometry) during a first period of time and to be directly controlled by a human surgeon (e.g., via a haptic telesurgical input console or other input device(s)) during a second period of time. Other applications, operations, and configurations of robotic surgical systems as described herein are anticipated.

It should be understood that the above embodiments, and other embodiments described herein, are provided for explanatory purposes, and are not intended to be limiting.

Further, the term "surgical intervention" as used herein should be understood broadly to include any activities applied toward the intentional modification of the anatomy of a human or animal body by the application of external forces and/or energies to the human or animal body; e.g., incision, ablation and/or cauterization by RF or other directed energies, excision, suturing, application of surgical adhesives, stapling, transplanting, cauterizing, sawing, abrading, applying a surgical fluid to (e.g., sterile, isotonic saline), cooling, heating, or any other surgical operation. Further "imaging," as applied to scanning or otherwise detecting information about biological tissues as described herein, could include generating two-dimensional images (e.g., camera images corresponding to one or more wavelengths of light reflected, scattered, refracted, or otherwise emitted from a surface), three-dimensional volumetric data (e.g., diffusion tensors, volumetric MM parameters, volumetric data generated through confocal imaging), or other types of data that describe the composition, geometry, anatomy, or other information about a surface, volume, or other region of a tissue. Correspondingly, an "image" generated via "imaging" could take the form of a two-dimensional image, three-dimensional volumetric data, or some otherwise organized data related to one or more properties of a biological tissue.

Additionally, systems and methods as described herein could be applied in applications other than surgical interventions. For example, systems and methods as described herein could be applied to toward the intentional modification of plant matter, non-living materials, and materials that were formerly alive for applications in, e.g., research, industry, construction, and food preparation and/or processing. In an example, systems and/or methods as described herein could be applied to the preparation of ex-vivo animal tissues (e.g., meat) in a food preparation application (e.g., to dissect or slice the meat, or according to some other application).

II. EXAMPLE SURGICAL ENVIRONMENTS, BIOLOGICAL TISSUES, AND ROBOTIC SURGICAL SYSTEMS

Robotic surgical systems and other systems as described herein could include a variety of components combined and/or configured in a variety of ways according to a variety of applications to allow the imaging of (e.g., the detection of information about) a biological tissue and to allow one or more surgical interventions (e.g., a dissection, a cauterization, an incision, an ablation, a retraction) to be performed on the biological tissue. FIG. 1A shows an example embodiment of a robotic surgical system 100 performing a surgical intervention on tissues of a person 105 at an intervention site 107. The robotic surgical system 100 includes an optical head 110 mounted on a first armature 120 configured to secure the optical head 110 in place relative to the intervention site 107. The optical head 110 is configured to optically image tissues at the intervention site 107 and to cut tissues at the intervention site 107 by exposing the tissues to beams of illumination having sufficient energy to ablate the tissue. The robotic surgical system additionally includes a retractor 130 mounted on a second armature 140. The retractor 130 is actuated to apply a force between and/or separate tissues opposite a cut or other hiatus in tissue.

Figure 1B:
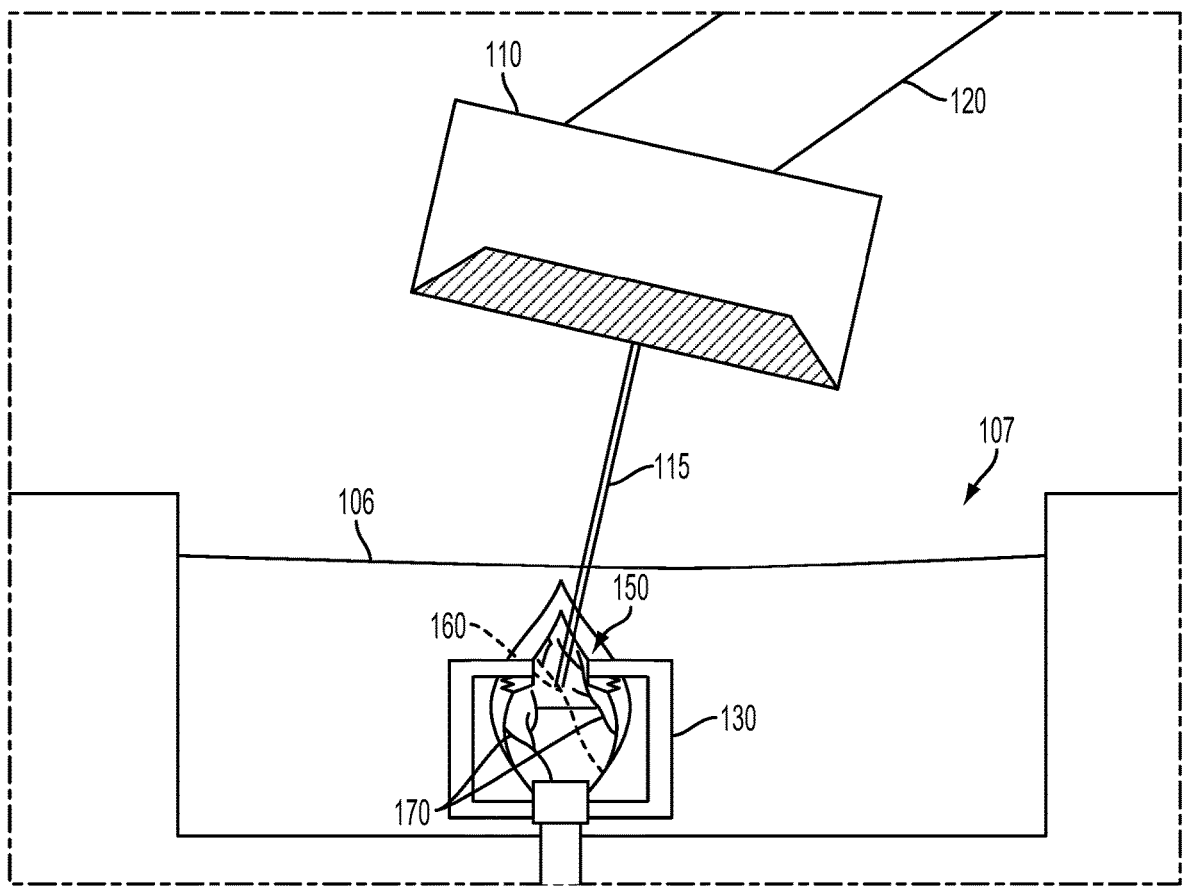
FIG. 1B illustrates a close-up view of the example surgical environment and example robotic surgical system of FIG. 1A.

FIG. 1B shows a close-up view of the intervention site 107. As illustrated in FIG. 1B, skin 106 of the person 105 is being retracted by the retractor 130 to expose underlying tissue. The underlying tissue is being cut along a cut trajectory 160 by a beam of illumination 115 emitted by a surgical laser of the optical head 110. Further, blood vessels 170 are present on the exposed tissue.

The optical head 110 includes a variety of components configured to image and to cut tissues at the intervention site 107. The optical head 110 includes one or more light-sensitive elements configured to receive light from the intervention site 107 to enable imaging of tissues. The optical head 110 additionally includes a surgical instrument in the form of a surgical laser configured to emit the beam of illumination 115 and to control at least an amplitude and a direction of the beam of illumination to cut tissue on a controlled fashion. The optical head 110 could additionally include other light sources configured to illuminate tissue in order to image the tissue or to enable some other application. The optical head 110 could include additional or alternative elements, e.g., additional or alternative surgical instruments configured to cut tissue or to perform some other function.

The optical head 110 could be operated to image biological tissues. This could include generating images, three-dimensional data, scanning surfaces, or generating some other data about the geometry, structure, contents, or other properties of tissues. Imaging could include operating one or more cameras to receive light (e.g., visible light, infrared light, ultraviolet light) at one more wavelengths or ranges of wavelengths to generate one or more two-dimensional images of the tissue. Imaging could include actively illuminating one or more portions of the tissue with light at one or more wavelengths. Imaging could include determining the presence, location, concentration, or some other information about an analyte in tissue (e.g., about the presence and location of cancer cells and/or one or more analytes indicative of cancer cells). Imaging could include determining three-dimensional information about the tissue, e.g., a three-dimensional description of the surface of the tissue, of boundaries or other features of or between tissues at the surface and/or within a biological tissue. Imaging could include generating some volumetric information about the tissue (e.g., determining a density, water content, or some other information throughout a volume of tissue using, e.g., CT, Mill, OCT).

In some examples, imaging could include illuminating the tissue, using a light source of the optical head 110, with light at a first wavelength and imaging the tissue using a camera configured to detect light at the first wavelength. Further, the first wavelength could be an excitation wavelength of a fluorophore present in the tissue, and the camera could be further configured to detect light at a second wavelength corresponding to an emission wavelength of the fluorophore. Such a light source and camera could be operated to image the presence, location or other information about the fluorophore in the tissue. The fluorophore could be naturally present in the tissue or could be introduced into the tissue (e.g., by being injected into the bloodstream of the person 105). The fluorophore could be part of and/or configured to selectively interact with a particular analyte (e.g., a cancer cell, an element of a cancer cell) such that imaging of the fluorophore could enable imaging of the analyte in the tissue.

In some examples, imaging the tissue could include detecting light from the tissue at a plurality of wavelengths and/or within a plurality of wavelengths. That is, one or more portions of tissue could be imaged spectrographically (e.g., using a spectrometer, using a hyperspectral imager). Additionally or alternatively, spectrographic imaging could include illuminating one or more portions of the tissue with light at a plurality of different wavelengths and detecting one or more properties (e.g., amplitude, spectral content) of light responsively emitted from the one or more portions of tissue. Spectrographic information about tissue could be used to determine a type of the tissue (e.g., muscle, tumor, neoplasm, nerve, blood vessel, tendon, skin), contents of the tissue (e.g., the presence of a fluorophore, cancer cells, or some other analyte), or some other property and/or health state of the tissue (e.g., a level of oxygenation by, e.g., detecting a change in the optical properties of hemoglobin in the tissue related to the oxygenation level of the tissue).

Active illumination could be used to scan the tissue over time (e.g., by illumination a plurality of spots, lines, or other-shaped tissues over time). This could be done to enable the imaging of a particular region of the tissue at a higher resolution, greater sensitivity, or some other property. Scanning individual regions of the tissue could enable imaging an area of tissue using a low-resolution light sensor (e.g., a single spectrometer, by detecting spectrographic content in light received from only a single region of tissue illuminated by a beam of light at a time). Additionally or alternatively, such scanning illumination could enable the determination of three-dimensional information about the tissue, e.g., the determination of the location, shape, and/or geometry of the surface of the tissue by illuminating particular portion of the tissue with a beam of light, imaging the light reflected from the tissue using a camera off-axis from the source of the illumination, and using triangulation or some other method to determine the location of the particular portion relative to the illumination source and/or camera.

Location and/or other three-dimensional information about the tissue could be detected in a variety of additional ways. Two or more cameras could be used to image the tissue and a shape and/or location of the tissue could be determined based on differences between images generated by the two or more cameras. A laser, ultrasonic, or other type of distance sensor could be used to determine an overall distance between the tissue and the distance sensor (i.e., a mean distance of portions of the tissue within some field of view) and/or a plurality of distances to particular portions of the tissue from the distance sensor to enable determination of a shape or other location information about the tissue. In some examples, a light source, surgical laser, or other element of the robotic surgical system 100 as described above could be operated to illuminate particular portions of tissue and, in combination with a camera imaging the tissue, the location of the portion of tissue (relative to the light source, laser, camera or other element(s) of the robotic surgical system 100) could be determined (e.g., by triangulation). Additionally or alternatively, a projector or other source of patterned light could operate to illuminate a region of tissue with one or more patterns of light (e.g., a grid) and the camera could image the pattern of illumination on the tissue to allow determination some location information (e.g., the location and shape of the surface of the tissue) about the tissue.

A robotic surgical system could operate based on information from additional imaging modalities. For example, a robotic surgical system could have access to volumetric information from CT scanners, MR imagers, confocal microscopes or other confocal optical sensors, optical coherence tomography (OCT) imagers, or other imaging systems. Such information could be generated prior to a surgical intervention (i.e., "pre-surgical" images) or could be generated one or more times during a surgical intervention. Such information could be generated by imagers that are part of and/or operated by the robotic surgical system 100; alternatively, such imagers could be separate systems in communication with the robotic surgical system 100. Conversely, imagers described herein as being part of a robotic surgical system could alternatively be part of a separate imaging system in communication with the robotic surgical system.

The optical head 110 is configured to cut tissue by applying a controlled beam of illumination having sufficient energy to ablate the tissue along a controlled trajectory. This could include emitting the beam from a surgical laser, e.g., a 2 micron laser, $CO_2$ laser, an excimer laser, or some other variety of laser configured to apply energy to a specified portion of a biological tissue. One or more properties of the surgical laser (e.g., a wavelength of light emitted by the laser, a power level, a beam width) could be specified and/or controlled according to an application. For example, a wavelength of light emitted by the surgical laser could be specified to preferentially heat water, fat, or some other element of tissue such that particular tissues are affected (e.g., ablated) by an emitted beam while other tissues (e.g., neighboring tissues, underlying tissues) are relatively unaffected. The location of tissue affected by an emitted beam could be controlled by controlling the direction of the emitted beam relative to the surgical laser and/or by controlling a location and/or orientation of the surgical laser.

In some examples, the optical head 110 or similar element of a robotic surgical system could include both a surgical laser and a light source configured to illuminate specified portion of a tissue (e.g., to image the tissue). Further, the surgical laser and light source could share some optical elements in common. For example, a beam emitted by the surgical laser and a beam emitted by the light source could pass through a lens, actuated mirror, filter, or some other optical element(s) such that the direction of the emitted beams could be controlled in common. This could enable, e.g., a high-fidelity match between the location of a tissue detected to contain a target to be ablated (e.g., cancer cells) and the location of a tissue responsively ablated by the surgical laser (e.g., because the common optical elements ensure that the output beams of the surgical laser and light source are substantially coincident).

As illustrated in FIG. 1A, the optical head 110 is disposed on an armature 120. The armature is configured to enable the secure positioning and orienting of the optical head 110 in space relative to the person 105, the intervention site 107, or some other element(s). This could include the armature being fixed in place (e.g., by one or more joints that are able to be manually and/or automatically secured). Alternatively, the armature could be actuated (e.g., could be a robotic armature with some number of degrees of freedom) to enable automatic and/or manually-specified positioning of the optical head 110. Such positioning could be performed at the beginning of a surgical intervention (e.g., to position the optical head proximate to the intervention site 107) and/or one or more times during a surgical intervention. This could be done automatically and/or by manual operation by a surgeon. Positioning during a surgical intervention could occur to adjust the view of a target tissue by an imager (e.g., to adjust for shifting and/or deformation of the tissue, due to occlusion of the target tissue and/or a region to be cut by other tissue or instruments, or according to some other application) and/or to make a target tissue accessible to one or more surgical instruments (e.g., within a 'field of view' of a surgical laser). The armature 120 could have a number of degrees of freedom and/or limits of operation according to an application. For example, the armature might enable only adjustment of the height of the optical head 110 over the intervention site 107. Alternatively, the armature could have six or more degrees of freedom such that the location and orientation of the optical head 110 relative to the intervention site 107 or other elements could be fully controlled. In some examples, a subset of the degrees of freedom of adjustment of the armature 120 could be automatically adjustable (e.g., electronically actuated); for example, the armature 120 could be configured to allow manual adjustment of the location of the optical head and automatic adjustment of the orientation of the optical head 110. Other configurations and/or operations of an armature configured to control the location and/or orientation of one or more elements (e.g., the optical 110 head) of a robotic surgical system (e.g., 100) are anticipated.

The robotic surgical system 100 could include additional or alternative surgical instruments. The robotic surgical system 100 could include additional or alternative surgical instruments configured to cut tissue. For example, the robotic surgical system 100 could include a scalpel including one or more sharpened edges configured to cut tissue. Such a scalpel could be disposed on an armature configured to control the location and/or orientation of the scalpel such that the robotic surgical system 100 could operate the armature to cut tissue using the scalpel according to some specified trajectory and/or desired dissection of the tissue. Such an armature could be mounted to the optical head 110 or to some other element(s) of the robotic surgical system 100 or could be mechanically independent (e.g., connected to a floor, table, ceiling, wall, or other element in a surgical suite). Additional or alternative cutting or other surgical instruments could be disposed on such an armature and operated to cut tissue according to an application. For example, a harmonic scalpel, an RF ablation probe, a thermal probe (e.g., a cryosurgical probe, a heat ablation probe), one or more electrodes of an electrosurgical and/or electrocautery system, or some other instrument could be disposed on such an armature and operated to cut tissue. One or more properties of such surgical instruments (e.g., an amplitude or frequency of vibration of a harmonic scalpel, a temperature or heat flux rate of a thermal probe, a voltage, current, frequency, polarity, or other property of operation of an RF ablation probe or electrosurgical and/or electrocautery system) could be controlled to control one or more properties of the dissection of a tissue (e.g., a rate of ablation, an amount of tissue ablated, a rate of dissection, a depth of dissection, an amount of heat applied to tissues neighboring a dissection).

Additional surgical instruments could be part of a robotic surgical system 100. In an example, the robotic surgical system 100 includes a retractor 130 having two blades configured to separate two portions of tissue. The portions of tissue could be opposite a dissection of the tissue (such dissection produced by the robotic surgical system 100 or by some other means), a hiatus (e.g., cleft or other separation)

between tissues, or related in some other way. The blades of the retractor could have one or more sharp and/or blunt prongs configured to secure tissue or be configured in some other way to attach to and/or apply forces to portions of tissue. In some examples, blades of a retractor could apply suction to or otherwise adhere to (e.g., by using a liquid and/or dry adhesive) to portions of tissue (e.g., portions of tissue within or proximate to a cut in the biological tissue) in order to apply separating forces to and/or control a displacement between the portions of tissue.

As illustrated, the retractor 130 is disposed on a second armature 140 configured to control one or more properties of the location and/or orientation of the retractor 130. The second armature 140 could be configured in a variety of ways as described herein (e.g., similarly to one of the configurations described for the first armature 120). Alternatively, the retractor could be self-retaining or otherwise configured to maintain position relative to a tissue without an armature or other securing means, and the retractor could be positioned by a surgeon (e.g., at a location indicated by the robotic surgical system 100, e.g., using a display, an augmented reality device, by illuminating an indicating pattern of light on the surface of tissue(s) at the intervention site 107 using, e.g., a light source of the optical head 110). The blades of the retractor 130 could be actuated (e.g., by a motor or some other actuator) and a force, distance, rate of separation, or other properties of the separation of tissues by the retractor could be controlled by the robotic surgical system 100. For example, the robotic surgical system 100 could operate the retractor 130 to expose the base of a dissection of the tissue, to improve the view and/or access of an imager, surgical instrument, or a surgeon to tissue(s) occluded by overlying tissue, to increase the width of a depth or otherwise high-aspect-ratio cut or hiatus in tissue, or according to some other application. Such operation could be performed based on one or more images of the tissue.

The robotic surgical system 100 could include additional elements (not shown). For example, the robotic surgical system 100 could include a communications interface to enable communications with one or more remote systems. For example, the communications interface could enable the operation of and/or receipt of imaging information from one or more imaging or other systems. In another example, the communications interface could enable the presentation of imaging or other information about the operation of the device to a remote system, e.g., a control console of a tele-surgical system. Further, the communications interface could enable complete or partial control of one or more elements of the robotic surgical system 100 by a remote system (e.g., by a control console of a tele-surgical system operated by a surgeon. Additionally or alternatively, the communications interface could be operated to receive information indicative of a desired dissection (e.g., an indication of the shape and/or location of one or more cuts or dissection to perform in a tissue, an indication of a target within a tissue to exposed and/or ablate) that could be achieved by the robotic surgical system 100.

The robotic surgical system 100 could include a user interface. The user interface could be operated to receive instructions from a surgeon or other user, e.g., to begin an automatic surgical intervention, to perform a particular surgical intervention, to achieve a specified desired dissection of tissue, to specify a target tissue to expose and/or ablate via dissection. In some examples, the user interface could be operated to indicate information to a surgeon about a prospective intervention (e.g., cut) to be performed by the robotic surgical system 100 and to receive input about the prospective intervention. For example, a number of prospective dissections of tissue could be presented to a surgeon for selection. In another example, the robotic surgical system 100 could determine that a prospective intervention has a chance of damaging sensitive tissues (e.g., blood vessels) and could request approval and/or information to modify of the prospective intervention before proceeding. In some examples, the user interface could be operated to receive a surgeon's approval before every prospective intervention (e.g., cut into tissue) performed by the robotic surgical system 100, or at some other regular or semi-regular interval. Additional operations of a robotic surgical system are anticipated.

A user interface could be configured to detect gestures of a user in space (e.g., using one or more cameras or other imagers). Such detected gestures could be used to inform some operation of the robotic surgical system 100, e.g., to indicate a desired dissection of tissue, to update a desired dissection, or some other application. In some examples, information indicative of a desired dissection could be detected by receiving information for a surgeon through a virtual reality and/or augmented reality interface, and interface (e.g., a haptic controller) of a control console of a tele-surgical system, or according to some other method. Such inputs could be received relative to an image of the tissue (e.g., relative to and in the space of a pre-surgical or other image of tissue).

The robotic surgical system 100 illustrated in FIG. 1 is configured to perform one or more surgical interventions as part of an 'open' surgical procedure. An 'open' surgical procedure includes any surgical procedures that include creating a large incision in the skin and/or some other overlying tissues and retracting said tissue in order to expose a target tissue or organ in order to perform some surgical intervention(s) on the target tissue or organ. In contrast, a 'closed' surgical procedure (e.g., an endoscopic procedure, a laparoscopic procedure, a thoracoscopic procedure) includes any surgical procedures some surgical intervention(s) are performed on a target tissue or organ located within a body cavity through one or more small holes into the body cavity. A robotic surgical system as described herein could be configured for the performance of a 'closed' surgical procedure. This could include elements of the system as described herein being disposed at the end of one or more rods or other elements configured to access the contents of a body cavity through a hole in the cavity (e.g., through a trocar or other elements adapted to provide a mechanical interface between the a rod or other element and tissues surrounding a hole into the body cavity).

An armature as described herein to control the location, orientation, or other properties of a camera, retractor, surgical instrument, or other element of a robotic surgical system could be disposed at the end of a rod (or other element of an endoscopic surgical instrument) to provide control of the location and/or orientation of the element of the robotic surgical system relative to the rod. Additionally or alternatively, an armature of a robotic surgical system as described herein could be configured to control the location and/or orientation of the element of the robotic surgical system by controlling the location and/or orientation of the rod (or other element of an endoscopic surgical instrument) on which the element is disposed. Other configurations and operations of a robotic surgical system and elements thereof to perform endoscopic, laparoscopic, thoracoscopic, or other types of 'closed' surgical procedures are anticipated.

The elements, configurations and operations thereof, and other descriptions of a robotic surgical system herein are intended as non-limiting, illustrative examples. A robotic surgical system could include additional or alternative elements configured similarly or differently than those described here. Further, system described herein could be operated according to the described applications or could be operated relative to some other application(s). For example, automated systems described herein to wholly or partially automatically dissect tissue based on imaging information about the tissue could additionally or alternatively be operated to automatically ablate a target tissue, suture tissue, apply a fluid (e.g., a drug, isotonic saline, a chemical agent) to a target tissue, cauterize a tissue and/or stop a blood flow from/within a tissue, permanently or temporarily block and/or ablate a nerve, blood vessel, lymphatic duct, or other structure, excise a tissue, amputate a limb, or some or surgical intervention of a human or animal tissue. Further automated system as described herein could be configured or operated to perform interventions on implants, surgical meshes, stents, electrodes, leads, or other foreign bodies on or within a human or animal tissue. Further, automated systems as described herein could be configure and/or operated to image and/or perform some interaction with or manipulation of objects outside of a surgical intervention. For example, automated systems as described herein could be used to automatically modify a fabric or other soft workpiece, e.g., to section a piece of fabric according to some desired dissection of the fabric. Additional applications of automated systems are anticipated.

III. EXAMPLE DISSECTIONS OF TISSUE

A robotic surgical system as described herein could be operated to automatically (i.e., with a minimum of human input) or semi-automatically (i.e., with regular or semi-regular input from a human, e.g., to approve and/or modify prospective surgical interventions to be performed by the robotic surgical system) perform a surgical intervention on a human. This generally includes dissection (i.e., cutting) of tissue. Dissection of tissue could be performed for a variety of reasons, including accessing a target region of tissue to remove, ablate, or otherwise interact with; accessing a damaged blood vessel, nerve, or other tissue to effect a repair or remediation of the tissue; access an organ or other tissue to remove for transplant; or some other application. Use of a robotic surgical system could allow such processes to be performed more quickly than by a human surgeon. Further, use of a robotic surgeon could allow for a reduced chance of infection as a result of a surgical intervention, due, e.g., to non-contact dissection of tissue (e.g., by a surgical laser), the ability to fully sterilize elements of the robotic surgical system coming into direct contact with the tissue (e.g., a scalpel disposed on an armature), and/or due to some other reason(s). Further, imaging information or other information about a dissection of tissue performed by a robotic surgical system could be recorded and used to enable some application, e.g., training of surgeons, improvement of algorithms used to control the robotic surgical system in future surgical interventions, to inform closing (i.e., suturing or otherwise restoring tissues dissected during a surgical intervention) of a wound or dissection created in the performance of a surgical intervention, or some other application.

A robotic surgical system could perform a surgical intervention on tissue by a number of methods and according to information indicating, in a variety of ways, a desired dissection or other outcome of the surgical intervention. A desired dissection could be indicated by information describing a particular surface in space, defined relative to an element of the robotic surgical system and/or a tissue or other elements of a person, to cut through the tissue. For example, a desired dissection could be described by information specifying a surgical plane or other boundary between specified tissues and/or specified regions of tissues. A desired dissection could be described by a location relative to a tissue to dissect into and/or a direction in which to dissect. Information describing a dissection could include information describing a target to fully or partially expose (e.g., a tumor located beneath an overlying tissue, a blood vessel, nerve, or other tissue to be repaired, ligated, or otherwise manipulated that is location beneath an overlying tissue). Information describing a dissection could also describe the location, shape, extent, or other information about tissues and/or regions of tissue not to dissect, e.g., nerves, blood vessels, ducts, tendons, important regions of cortex, or some other specified regions of tissue.

Figure 2A:
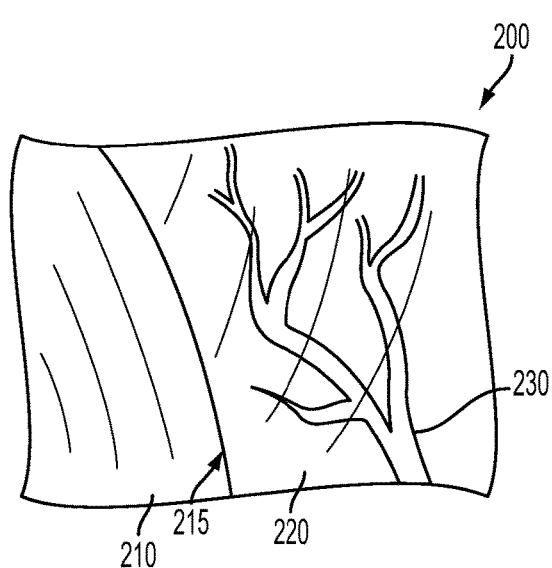
FIG. 2A illustrates a surface view of an example biological tissue in a surgical environment.
Figure 2B:
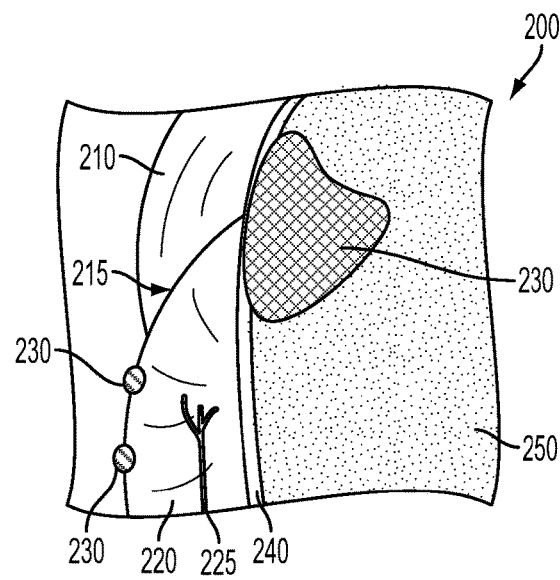
FIG. 2B illustrates a cross-sectional view of the example biological tissue of FIG. 2A.

To illustrate a variety of described dissections of tissue, FIGS. 2A and 2B illustrate surface and cross-sectional views, respectively, of an example region of tissue 200. The example tissue 200 includes first 210 and second 220 muscles separated by a surgical plane 215 (i.e., a sheet or other thin layer of connective tissue that is more easily dissected and/or could be dissected with less bleeding than a dissection of neighboring tissues). Note that a surgical plane, as described herein, does not necessarily refer to a flat, two-dimensional surface (as in the mathematical definition of 'plane'). Rather, a surgical plane can be a surface taking any shape defined by an interface between two or more tissues. A blood vessel 230 is located on the surface of the tissue 200. Beneath the muscles 210, 220 is a basement membrane 240 (e.g., a region of connective tissue, a layer of epithelial tissue separating compartments of a body containing the tissue 200, a bursa or other lubricating fluid-filled sac) separating the muscles 210, 220 from deeper tissue 250. The tissue 200 additionally includes a target tissue 230 (e.g., a tumor, a cyst, a region of cardiac muscle allowing for re-entrant electrical conduction, an epileptogenic region of nervous tissue). A nerve 225 is located within the second muscle 220.

Figure 2C:
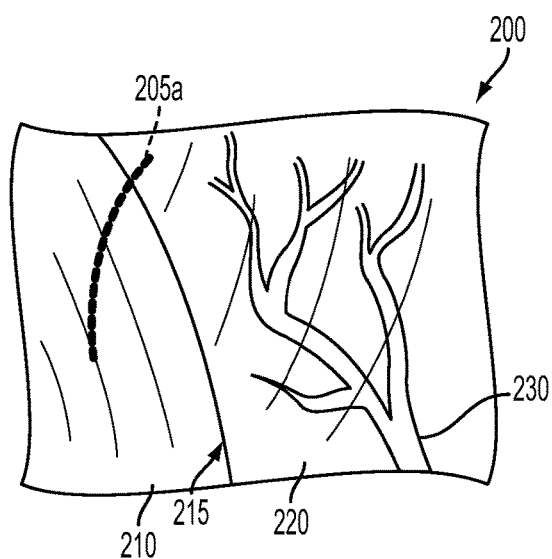
FIG. 2C illustrates a surface view of an example desired dissection of the biological tissue of FIGS. 2A and 2B.
Figure 2D:
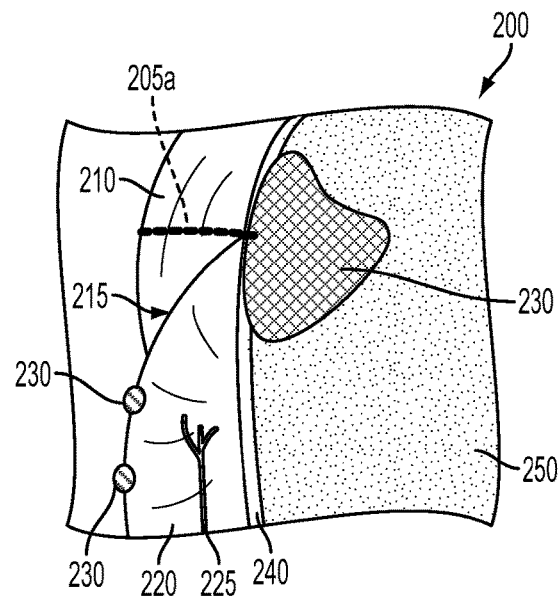
FIG. 2D illustrates a cross-sectional view of the example desired dissection of FIG. 2C.

Information indicating a desired dissection could specify a particular surface, manifold, or other three- or two-dimensional shape defined relative to the tissue 200 and/or a feature of the tissue 200, an imager or other element of a robotic surgical system, a fiducial or other marker location on or within the tissue 200, or according to some other absolute or relative location measurement system. As an example, FIGS. 2C and 2D illustrate surface and cross-sectional views, respectively, of the example region of tissue 200 with a first desired dissection 205a that could be indicated and/or specified as described herein. The first desired dissection 205a is a curved surface that describes a dissection of the tissue 200 through the muscles 210, 220 and basement membrane 240 to wholly or partially expose the target tissue 230. The first desired dissection 205a could have a location and/or orientation specified relative to a feature of the tissue, a fiducial or marker on or within the tissue, a location of one or more elements (e.g., an imager) of the robotic surgical system, or some other element(s).

In some examples, a desired dissection could be indicated by information describing a particular feature or aspect of a tissue (e.g., 200). For example, information indicating a desired dissection could describe a particular surgical plane between two more tissues and/or regions of tissue. This could include describing the shape, location or other properties of the two or more tissues. For example, information indicating a desired dissection could define differences in a spectrographic response between two or more tissues such that the robotic surgical system could determine the location of the desired dissection relative to the tissues by detecting a border between regions having spectrographic responses corresponding to the described difference in spectrographic responses. Alternatively, properties of a connective tissue location along the boundary between the two tissues. In another example, the desired dissection could be described as a location and shape of the boundary between the two or more tissues, and a robotic surgical system could operate to dissect that boundary and/or to update the boundary (based on imaging information about the tissues) according to translations, deformations, retractions, or other changes in the tissues.

Figure 2E:
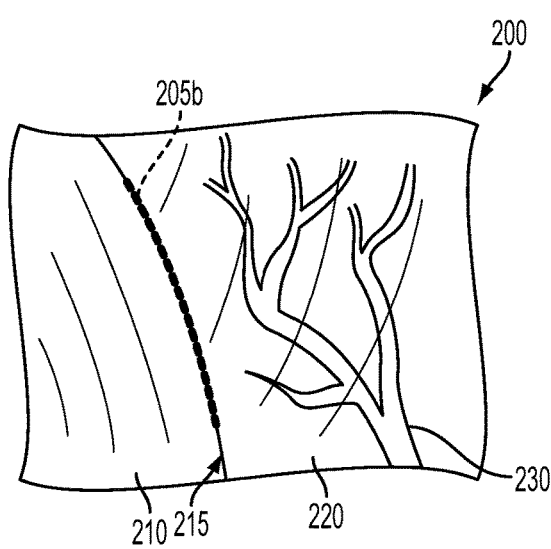
FIG. 2E illustrates a surface view of an example desired dissection of the biological tissue of FIGS. 2A and 2B.
Figure 2F:
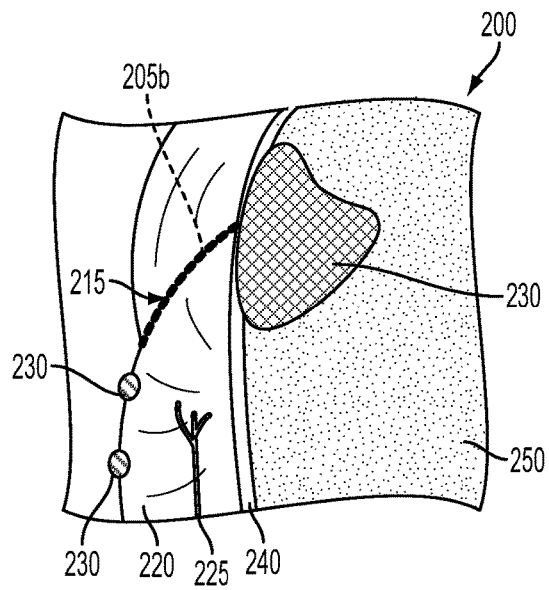
FIG. 2F illustrates a cross-sectional view of the example desired dissection of FIG. 2E.

As an example of a desired dissection following a surgical plane or other boundary between two or more tissues, FIGS. 2E and 2F illustrate surface and cross-sectional views, respectively, of the example region of tissue 200 with a second desired dissection 205b that could be indicated and/or specified as described herein. The second desired dissection 205b is a curved surface that describes a dissection of the tissue 200 along the surgical plane 215 between the muscles 210, 220 and through the basement membrane 240 to wholly or partially expose the target tissue 230.

Information indicating a desired dissection could be determined by, generated by, input into, and/or received by a robotic surgical system via a variety of methods. In some examples, the information indicating the desired dissection could be indicated by a user relative to some pre-surgical image of a tissue. The user could indicate a specific desired dissection (e.g., a specific shape, location, direction, or other information describing one or more properties of a desired dissection relative to the pre-surgical image). Additionally or alternatively, the user could indicate a target tissue within the pre-surgical image to expose and/or ablate, a number of tissue to avoid (e.g., nerves, blood vessels, sensitive tissues, or other 'avoidance targets').

Figure 2G:
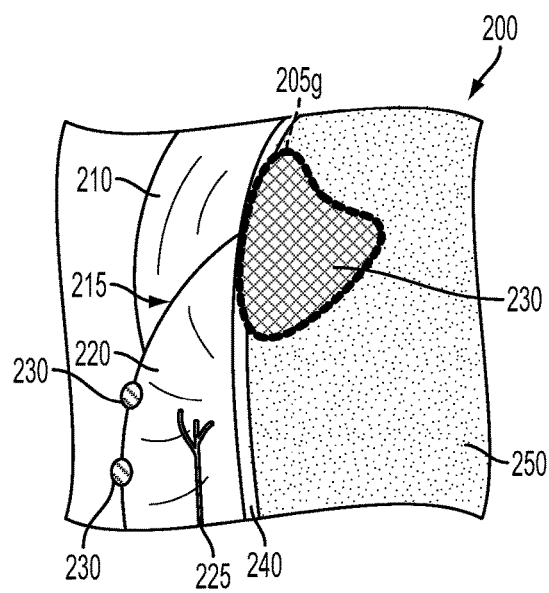
FIG. 2G illustrates a cross-sectional view of an example desired dissection of the biological tissue of FIGS. 2A and 2B comprising indication of a target tissue to be exposed.
Figure 2H:
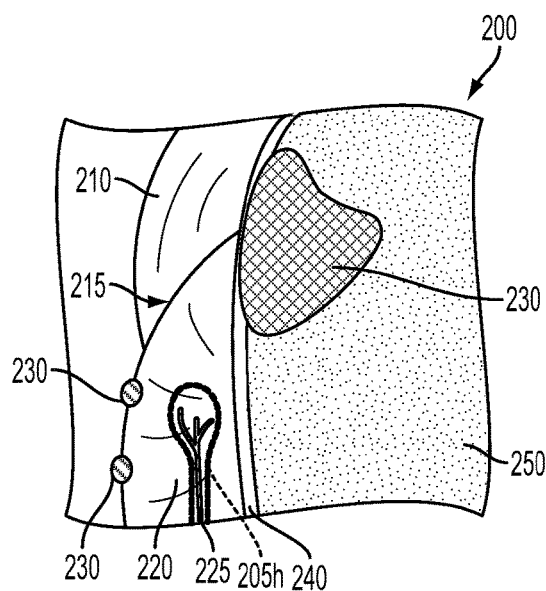
FIG. 2H illustrates a cross-sectional view of an example desired dissection of the biological tissue of FIGS. 2A and 2B comprising indication of a target tissue to be avoided.

As an example of such targets indicated by a user, FIGS. 2G and 2H illustrate cross-sectional views of the example region of tissue 200. FIG. 2G illustrates a target indication 205g that indicates the location and shape of the target tissue 230. The target indication could be part of and/or used to determine some information indicative of a desired dissection of the tissue 200. FIG. 2H illustrates an avoidance indication 205h that indicates the location and shape of an avoidance target containing the nerve 225. The target indications 205g, 205h could be specified by a user (e.g., using a touchscreen, an augmented reality system, a control console of a tele-surgical system), generated by a processor or other computing device, e.g., though automated image analysis, or through a combination of user input and processor-generated information.

Further information indicating a desired dissection (e.g., a location and shape of a desired dissection of the tissue relative to the tissue, an imager, etc.) could be determined from information describing targets, avoidance targets, or other aspects of a tissue. For example, a robotic surgical system or other computing device could receive a description of a target tissue and, based on a pre-surgical and/or one or more intra-surgical images of the tissue, determine a desired dissection of the tissue to wholly or partially expose the target and/or achieve some other goal relative to the target. Such a determination could include specifying a desired dissection to minimize bleeding, tissue trauma, time for post-operative care and/or rehabilitation, and/or relative to some other consideration. For example, the robotic surgical system or other computing device could determine a desired dissection that follows one or more surgical planes within a tissue to wholly or partially expose the target tissue. Additionally or alternatively, such a determination could generate a desired dissection to avoid one or more specified avoidance targets.

Further, information specifying the location, shape or other information about a target tissue and/or an avoidance target could be determined by a robotic surgical system or other computing device based, e.g., on a pre-surgical or other type of image of the tissue. For example, a robotic surgical system could determine the location within a tissue of blood vessels having a size above a certain threshold and nerves within a tissue, and determine some information indicative of a desired dissection that includes indications of the determined locations. In another example, a robotic surgical system could determine the location of a target tissue (e.g., a tumor, a cyst, an aneurism, a stenosis, an adhesion, a tissue containing cancer cells) within a pre-surgical or other type of image of the tissue (e.g., by matching a shape, density, or other information about a target tissue to a corresponding region in the image of the tissue).

Note that the example region of tissue 200, example shapes and/or location of desired dissections and/or descriptions of information indicative of desired dissection described herein are intended to illustrate by example and are not intended to be limiting. Other methods of indicating and/or describing desired dissection of tissue are anticipated. Further, additional or alternative methods of identifying the contents and/or properties of a portion of a tissue and/or determining a desired dissection and/or information indicative thereof by a computational device and/or indication of such by a human user are anticipated.

Information indicative of a desired dissection could include descriptions of the location of shapes of target regions within a tissue (e.g., regions containing a target to expose, ablate, or otherwise manipulate; regions containing sensitive tissues that should not be dissected, incised, or ablated), shapes and/or locations of desired dissections relative to features or aspects of a tissue, properties of tissue to ablate (e.g., connective tissue of a surgical plane) and/or to ablate between in order to achieve a dissection along a surgical plane, or other information describing in whole or in part the shape, location, or other properties of a described dissection of a tissue. A desired dissection and/or information indicative thereof could be indicated and/or determined before a surgical intervention (e.g., based on a pre-surgical image of a tissue), at the beginning of a surgical intervention (e.g., based on an initial surgical image of the tissue), and/or modified during the performance of a surgical intervention. For example, a deformation, translation, or other change in a tissue could be determined based on one or more images of or other information about the tissue, and information indicative of a desired dissection (e.g., a location and shape of the desired dissection) could be updated according to the one or more images or other information (e.g., according to a correspondence between the shape and location of the tissue in an image corresponding to an initial desired dissection and the deformed, translated, or otherwise changed shape and location of the tissue in the one or more images). Additionally or alternatively, information indicative of a desired dissection (e.g., a location and shape of the desired dissection) could be updated according to input from a surgeon during a surgical intervention (e.g., according to the presence and/or translation or deformation of an obstacle, target, and/or avoidance target in the tissue).

IV. EXAMPLE OPERATION OF A ROBOTIC SURGICAL SYSTEM

A robotic surgical system could be operated in a variety of ways according to information describing a desired dissection of a biological tissue to achieve the described dissection of biological tissue. Generally, a robotic surgical system can operate to repeatedly image a biological tissue, determine an operation (e.g., a cut of the tissue) based on an image of the biological tissue and some information indicative of a desired dissection, and execute the determined operation. In some examples, determining an operation could include updating information indicative of the desired dissection (e.g., updating an indicated shape and location of a dissection according to a correspondence between a current image of the tissue and a previous image of the biological tissue), determining an operation of a surgical instrument (e.g., a scalpel, a surgical laser) to cut tissue and/or adjusting one or more properties of an ongoing operation of such a surgical instrument to cut tissue, or determining some other operation. In some examples, determining an operation could include determining that user input is necessary to continue operation of the robotic surgical system.

A robotic surgical system could be operated to receive and/or determine information indicative of a desired dissection of a biological tissue. The robotic surgical system could then receive an initial image the biological tissue (e.g., by operating an imager of the robotic surgical system), determine an initial trajectory of a surgical instrument to cut the biological tissue, and control the surgical instrument according to the initial trajectory such that the surgical instrument makes an initial cut into the biological tissue.

After operating the surgical instrument to make the initial cut into the biological tissue, the robotic surgical system could receive a subsequent image of the biological tissue (e.g., by operating an imager of the robotic surgical system) that shows the initial cut and at least a portion of the biological tissue surrounding the initial cut. Based on the subsequent image and the information indicative of the desired dissection, the robotic surgical system could determine whether the initial cut has achieved the desired dissection. Responsive to determining that the initial cut has not achieved the desired dissection, the robotic surgical system could determine one or more subsequent trajectories of the surgical instrument to cut into the biological tissue and could control the surgical instrument based on the one or more subsequent trajectories to make one or more subsequent cuts into the biological tissue. The depth of a subsequent cut, relative to a preceding (e.g., initial) cut could be increased by, e.g., increasing a power of a beam of light emitted by a surgical laser, increasing a force applied to a scalpel by an armature, increasing a voltage and/or current applied to a probe or electrode, or by some other means such that the total depth of a cut, after performance of such a subsequent cut, is approximately equal to the depth of a desired dissection.

Note that the above operations could be performed a plurality of times, and description of cuts, images, and trajectories as 'subsequent' could refer to a particular cut, image, or trajectory during a first iteration. The particular cut, image, or trajectory, during a second iteration subsequent to the first, could be described during the second iteration as 'initial.' For example, a particular 'subsequent' image received during a first iteration of the operations above and used to determine whether a cut has achieved a desired dissection of tissue could also be, during a second iteration, an 'initial' image used to determine an 'initial' trajectory during the second iteration.

In some examples, the initial trajectory could be specified so as not to achieve the complete desired dissection; that is, the initial trajectory could specify a short and/or shallow cut, such that any changes in the biological tissue (e.g., deformation or translation of the tissue due to external forces, the action of the robotic surgical system) could be compensated for by receiving a subsequent image, and generating a related, 'updated' subsequent trajectory before the development of a significant deviation between an initial image of the tissue (and an initial trajectory developed therefrom) and the state of the actual biological tissue. Additionally or alternatively, the robotic surgical system could, while controlling the surgical instrument to make the initial cut, receive a plurality of images of the biological tissue over time (e.g., at a high frequency, e.g., 10s to 100s of Hertz) and could responsively update the initial trajectory in response to one or more of the plurality of images. Such imaging and responsive updating could increase the safety and/or accuracy of operation of the robotic surgical system to dissect tissue according to a determined trajectory or other specification by allowing for adaptation of the operation of the robotic surgical system to changes (e.g., translations, deformations) in a target biological tissue in nearly real-time.

Figure 3A:
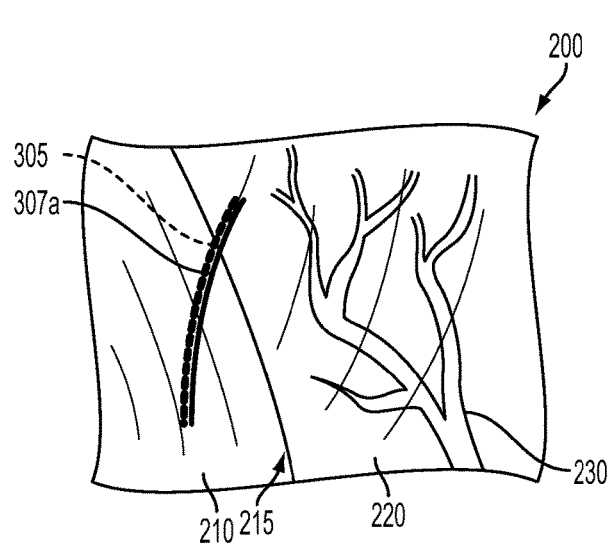
FIG. 3A illustrates a surface view of an example desired dissection of the biological tissue of FIGS. 2A and 2B and a related initial trajectory.
Figure 3B:
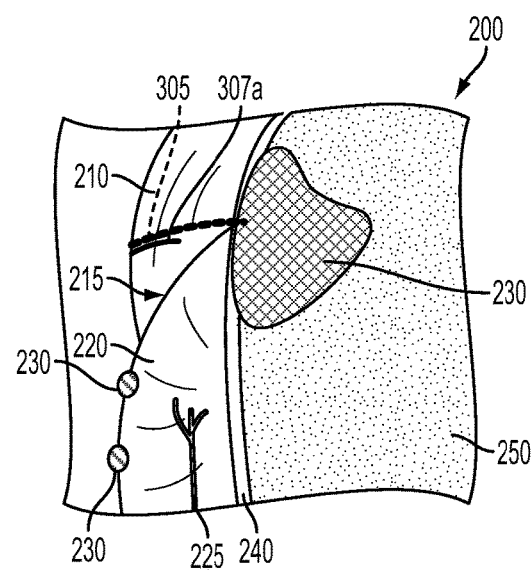
FIG. 3B illustrates a cross-sectional view of the example desired dissection and initial trajectory of FIG. 3A.

To illustrate the relationship between a desired dissection and a trajectory determined based on information indicating such a desired dissection, FIGS. 3A and 3B illustrate surface and cross-sectional views, respectively, of the example region of tissue 200 with a desired dissection 305 that could be indicated and/or specified as described herein. Also illustrated is a first trajectory 307a related to the desired dissection 305. The first trajectory 307a describes a surface that is substantially coincident with an outer portion (i.e., a portion proximate to the surface of the tissue 200) of the desired dissection. A surgical instrument (e.g., a scalpel) could be operated to intersect a cutting surface or other dissection aspect of the surgical instrument (e.g., an ablating thermal or electrical probe of a thermal and/or electrical surgical instrument) with the surface defined by the first trajectory 307a.

Figure 3C:
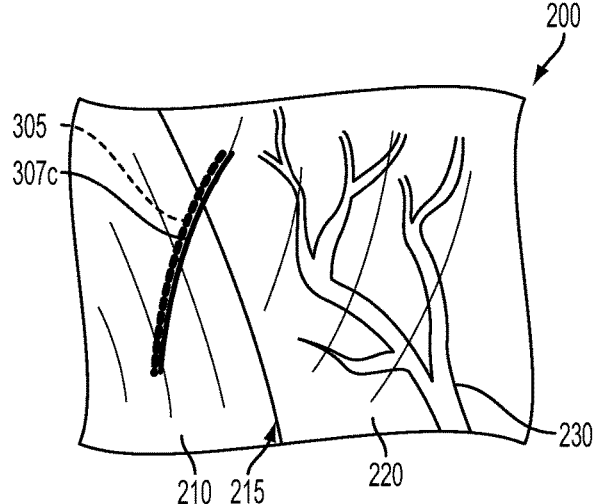
FIG. 3C illustrates a surface view of an example desired dissection of the biological tissue of FIGS. 2A and 2B and a related initial trajectory.
Figure 3D:
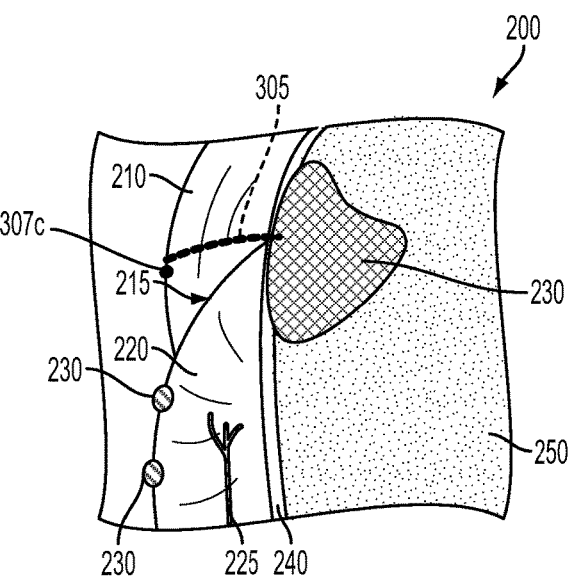
FIG. 3D illustrates a cross-sectional view of the example desired dissection and initial trajectory of FIG. 3C.

A trajectory determined from information indicating a desired dissection could describe a line or other shape on the surface of a tissue that could be dissected by a surgical instrument to wholly or partially achieve a desired dissection of the tissue. FIGS. 3C and 3D illustrate surface and cross-sectional views, respectively, of the example region of tissue 200 with a desired dissection 305 that could be indicated and/or specified as described herein. Also illustrated is a second trajectory 307c related to the desired dissection 305. The second trajectory 307c describes a line on the surface of the biological tissue that is substantially coincident with the intersection of the desired dissection with the surface of the tissue 200. A surgical instrument (e.g., a surgical laser) could be operated to emit a beam of energy along the second trajectory 307c.

Figure 3E:
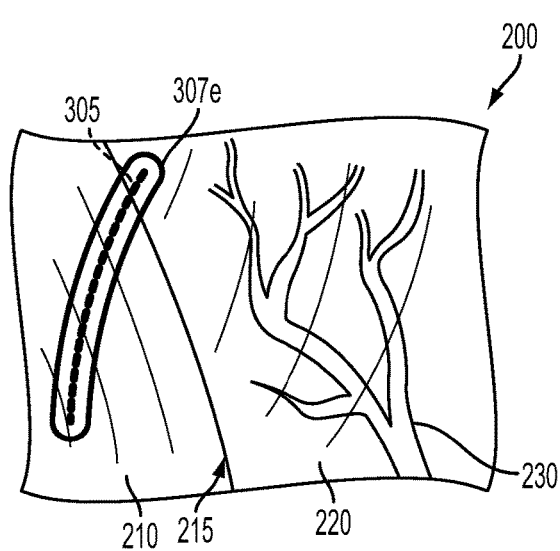
FIG. 3E illustrates a surface view of an example desired dissection of the biological tissue of FIGS. 2A and 2B and a related initial trajectory.
Figure 3F:
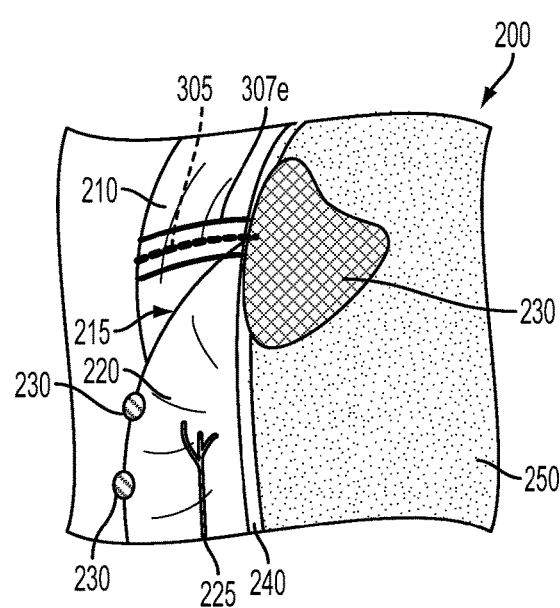
FIG. 3F illustrates a cross-sectional view of the example desired dissection and initial trajectory of FIG. 3E.

A trajectory determined from information indicating a desired dissection could describe a volume of tissue that could be ablated, resected, or otherwise removed by a surgical instrument to wholly or partially achieve a desired dissection of the tissue. FIGS. 3E and 3F illustrate surface and cross-sectional views, respectively, of the example region of tissue 200 with a desired dissection 305 that could be indicated and/or specified as described herein. Also illustrated is a third trajectory 307e related to the desired dissection 305. The third trajectory 307e describes a volume of the biological tissue that encloses the desired dissection. A surgical instrument (e.g., a surgical laser, an electrosurgical probe, an electrocautery probe, an RF ablation probe) could be operated to ablate tissue within the third trajectory 307e. This could include controlling an energy output (e.g., a beam intensity of a laser, a current, frequency, and/or voltage of an electrosurgical probe, an electrocautery probe, or an RF ablation probe) of the surgical instrument to ablate a region of tissue matching the width, depth, or other properties of the volume defined by the third trajectory 307e.

The robotic surgical system could perform other determinations and/or operations based on one or more images of the biological tissue. For example, the robotic surgical system could update the information indicative of the desired dissection and/or an initial or other determined trajectory based on one or images of the biological tissue. The robotic surgical system could operate a retractor and/or translate or rotate one or more elements of the robotic surgical system to improve access (e.g., by a surgical instrument, by an imager) to regions of the biological tissue (e.g., to tissues at the base of a cut or other dissection or cleft in the tissue). The robotic surgical system could operate to perform some additional surgical intervention once a desired dissection has been achieved, e.g., ablating a target (e.g., a tumor) that has been exposed by achieving the desired dissection. Additional operations of a robotic surgical system, and alternative implementations of operations of a robotic surgical system as described herein, are anticipated.

In some examples, the robotic surgical system could update a description of a desired dissection based on images of the biological tissue. For example, information indicative of a desired dissection of the biological tissue could include a pre-surgical image of the biological tissue and a description of the desired dissection (e.g., a shape and location of the desired dissection) defined relative to the pre-surgical image. Determining an initial trajectory (or a subsequent trajectory) of the surgical instrument to cut the tissue could include updating the description of the desired dissection based on a correspondence between the pre-surgical image and an initial image of the biological tissue, and determining the initial trajectory based on the updated description of the desired dissection.

Figure 4A:
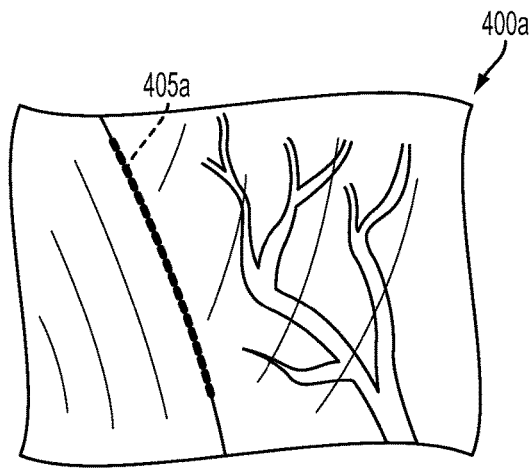
FIG. 4A illustrates a surface view of an example biological tissue in a surgical environment and an example desired dissection thereof.
Figure 4B:
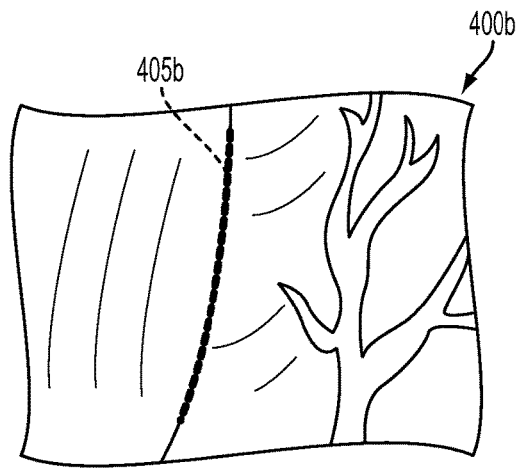
FIG. 4B illustrates the example biological tissue of FIG. 4A, having been deformed, and an updated desired dissection thereof.

To illustrate such updating, FIG. 4A illustrates a pre-surgical image of a biological tissue 400a. FIG. 4A additionally illustrates a first desired dissection 405a of the biological tissue, defined relative to the pre-surgical image 400a. FIG. 4B illustrates an initial image 400b of the biological tissue (i.e., an image taken of the biological tissue immediately before and/or during a surgical intervention). The biological tissue, as represented by the initial image 400b, has rotated, shifted, deformed, or otherwise changed relative to its state and/or orientation represented in the pre-surgical image 400a. A second desired dissection 405b is defined relative to the initial image 400b. A description of the second desired dissection 405b could be determined based on the description of the first desired dissection 405a and a correspondence between the pre-surgical image and the initial image (e.g., a warping or other deformation of the description of the first desired dissection based on the locations of corresponding features of the pre-surgical 400a and initial 400b images of the biological tissue).

Such changes in images taken of the same biological tissue could be due to a difference between the location and/or orientation of an imager configured to take the pre-surgical image relative to the biological tissue and the location and/or orientation of an imager configured to take the initial image relative to the biological tissue. Such changes could additionally or alternatively be due to a deformation, manipulation, or other change in state of the biological tissue between a period of time when the pre-surgical image was taken and a period of time when the initial image was taken. Such changes in state could be due to a surgical intervention (e.g., a dissection, retraction, ablation, or other processes performed on the biological tissue and/or an overlying biological tissue like skin that has been dissected and retracted to expose the biological tissue), changes in orientation and/or shape due to the force of gravity, or changes due to a change in posture or some other changes in the anatomy of a person or other subject of a surgical intervention as described herein.

Note that, while the above process of updating a description of a desired dissection based on images of a biological tissue is described as relating to correspondences between a pre-surgical and an initial image, such an updating of a description of a desired dissection could be performed based on a correspondence between pairs of images of a biological tissue taken at different times. For example, such an updating process could be performed between an initial image and a subsequent image of a biological tissue taken as part of the operation of a robotic surgical system to implement a surgical intervention. Similarly, other information indicative of a desired dissection (e.g., a description of an avoidance target, a description of a target tissue) could be updated based on a correspondence between two or more images of a biological tissue.

Figure 5A:
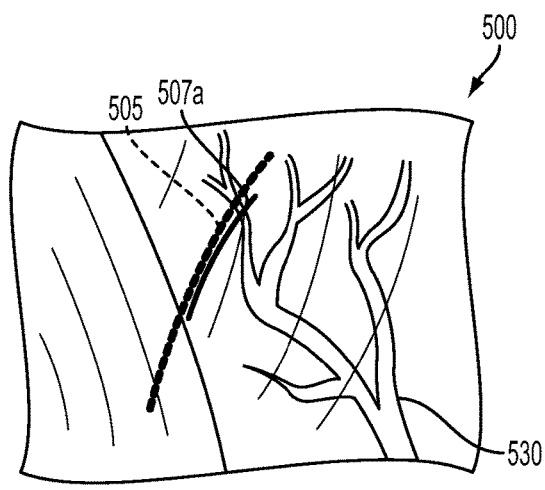
FIG. 5A illustrates a surface view of an example desired dissection of the biological tissue of FIGS. 2A and 2B and a related initial trajectory.
Figure 5B:
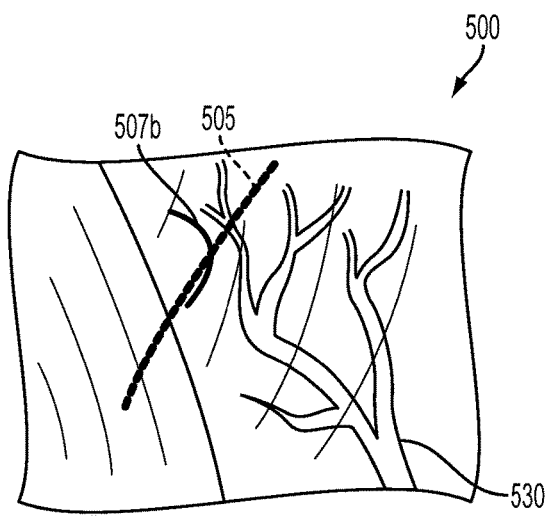
FIG. 5B illustrates a surface view of the example desired dissection of FIG. 5A and an updated initial trajectory.

The robotic surgical system could additionally operate to detect obstacles (e.g., blood vessels, tendons, nerves) in the biological tissue and to perform some determination and/or operation responsive to such a determination. As an example, FIGS. 5A and 5B illustrate a biological tissue 500 and a desired dissection 505 of the biological tissue. The biological tissue includes an obstacle 530 (i.e., a blood vessel). A first trajectory 507a describing the operation of a surgical instrument to cut the biological tissue 500 is illustrated in FIG. 5A and could be determined based on an image of the biological tissue 500. The first trajectory 507a intersects the obstacle 530. The robotic surgical system could determine, based on an image of the biological tissue 500, the presence, shape, and/or location of the obstacle 530. Further, the robotic surgical system could determine that the first trajectory 507a intersects and/or comes within a specified distance of the obstacle 530. Responsive to such a determination, the robotic surgical system could update the first trajectory 507a to determine a second trajectory 507b to avoid the location of the obstacle. Additionally or alternatively, such processes could be performed relative to the shape and/or location of an avoidance target described as part of information indicative of the desired dissection 505.

Figure 6A:
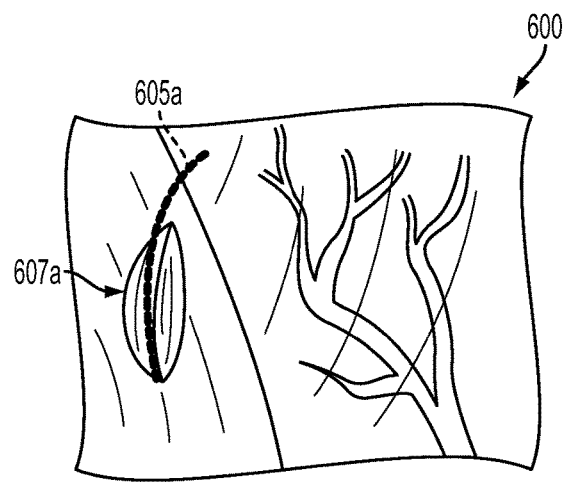
FIG. 6A illustrates a surface view of an example biological tissue that has been cut in a surgical environment and an example desired dissection thereof.
Figure 6B:
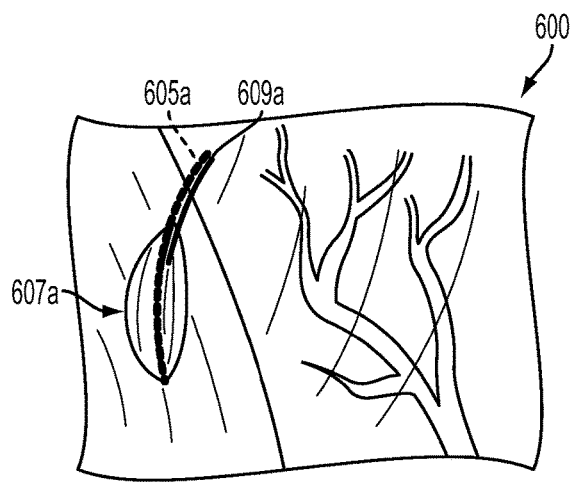
FIG. 6B illustrates the example biological tissue and dissection thereof of FIG. 6A and a subsequent trajectory.
Figure 6C:
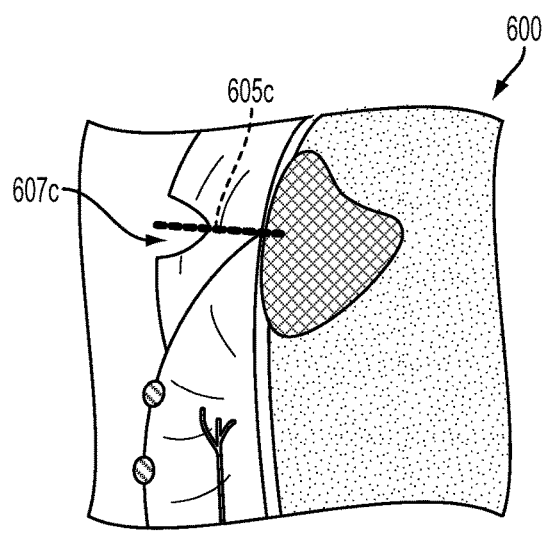
FIG. 6C illustrates a cross-sectional view of an example biological tissue that has been cut in a surgical environment and an example desired dissection thereof.
Figure 6D:
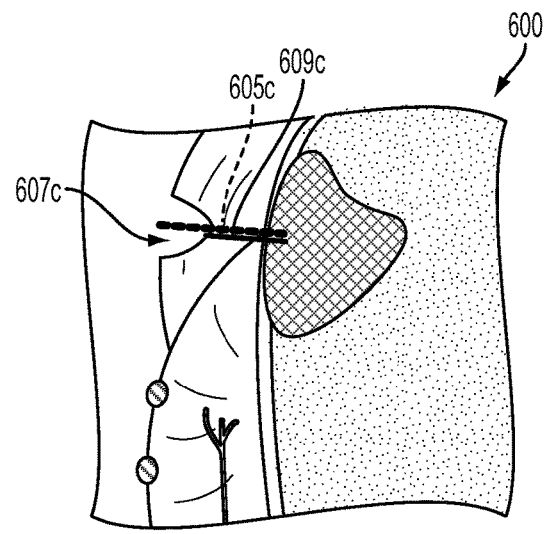
FIG. 6D illustrates the example biological tissue and dissection thereof of FIG. 6B and a subsequent trajectory.

The robotic surgical system could, based on one or more images of a biological tissue, determine that a desired dissection has not been achieved. Responsive to such a determination, the robotic surgical system could determine one or more subsequent trajectories that could be used to operate a surgical instrument to wholly or partially achieve the desired dissection. For example, a cut performed by the robotic surgical system (or by some other means) could be insufficiently long. As an illustrative example, FIGS. 6A and 6B illustrate a biological tissue 600 that has been cut (i.e., that includes a first cut 607a). Also illustrated in FIGS. 6A and 6B is a desired dissection 605a of the biological tissue 600. FIG. 6B also illustrates a first subsequent cut 609a that could be determined and that could be used to control a surgical instrument to achieve the desired dissection. In another example, a cut performed by the robotic surgical system (or by some other means) could be too shallow. As an illustrative example, FIGS. 6C and 6D illustrate a biological tissue 600 that has been cut (i.e., that includes a second cut 607c). Also illustrated in FIGS. 6C and 6D is a desired dissection 605c of the biological tissue 600. FIG. 6D also illustrates a second subsequent cut 609c that could be determined and that could be used to control a surgical instrument to achieve the desired dissection.

In some examples, an imager, a surgical instrument (e.g., a surgical laser), or some other optical element of the robotic surgical system could have a field of view. That is, the optical element could be able to illuminate and/or receive illumination from a specified region (e.g., a cone or other-shaped region representation a set of angles relative to, e.g., an aperture of the optical element) such that the optical element is only able to illuminate and/or receive light from objects (e.g., biological tissues) within the specified region. Further, the field of view of the optical element could be limited by objects within the field of view; that is, the optical element could be substantially unable to illuminate and/or receive light from first objects that are occluded by other objects interposed between the imager and the first objects. The robotic surgical system could determine that the field of view of an optical element does not include a target region (e.g., the base of a cut in a biological tissue, a region containing a cut trajectory to be cut by a surgical instrument). Responsive to such a determination, the robotic surgical system could operate an armature or other actuator (s) to adjust the location and/or orientation of the optical element such that the target region is within the field of the view of the optical element.

As an illustrative example, FIGS. 7A and 7B show a biological tissue 700 that has an initial cut 725. FIGS. 7A and 7B additionally illustrate a camera 705 configured to image the biological tissue. As illustrated in FIG. 7A, the camera is unable to image biological tissue on both sides of the initial cut 725. A robotic surgical system that includes the camera 705 could, based on an image generated using the camera 705, determine that the camera 705 is unable to image biological tissue on both sides of the initial cut 725 (e.g., by determining that an image generated by the camera 705 does not show the biological tissue on both sides of the initial cut 725). Responsive to this determination, the robotic surgical system could control an armature or other actuator connected to the camera 705 to position the camera 705 as shown in FIG. 7B to provide a view of the biological tissue on both sides of the initial cut 725. Additionally or alternatively, the robotic surgical system could indicate to a human a re-positioning of the camera 705 that could provide a view of biological tissue on both sides of the initial cut 725, and the human could reposition the camera 705.

Additionally or alternatively, access to the base of a cut or some other occluded or hard-to-access region of a biological tissue could be provided by retracting portions of the biological tissue using one or more retractors. A retractor, as described elsewhere herein, could be operated by a robotic surgical system to apply a separating force between two or more portions of tissue to separate the two or more portions of tissue and to provide access to tissue locations deep relative to the two or more portions of tissue. Access to a region of tissue could include the ability illuminate and/or receive light from the region of tissue (e.g., the ability to image the region of tissue, the ability to heat, cauterize, ablate, or otherwise manipulate or modify the region of tissue using a beam of illumination emitted from a surgical laser or similar surgical instrument). Access to a region of tissue could include the ability of an actuated scalpel, harmonic scalpel, thermal probe, RF probe, electrosurgical probe, electrocautery tool, or other actuated surgical instrument to contact the region of tissue.

As an illustrative example, FIGS. 8A and 8B show a biological tissue 800 that has an initial cut 825. As illustrated in FIG. 8A, portions of tissue opposite the initial cut 825 could be separated (e.g., by a retractor) to improve access (e.g., of a surgical instrument) to biological tissue at the base of the initial cut 825. A robotic surgical system could, based on one or more images of the biological tissue generated using a camera or other imaging system, determine that portions of biological tissue opposite the initial cut 825 could be separated by a retractor to improve access (e.g., of a surgical instrument of the robotic surgical system, of an imager of the robotic surgical system) to biological tissue at the base of the initial cut 825. Responsive to this determination, the robotic surgical system could control an armature or other actuator connected a retractor of the robotic surgical system (illustrated in FIG. 8B as two blades 850) to position the retractor (e.g., to position the blades 850 of the retractor) between the portions of biological tissue opposite the initial cut 825. The robotic surgical system could then control the retractor (e.g., by operating a motor or other actuator configured to separate and/or apply a separating force between the blades 850 of the retractor) to apply a separating force between the portions of biological tissue opposite the initial cut 825.

Further, the robotic surgical system could periodically or continuously monitor some property related to the retractor (e.g., a separation of the portions of biological tissue opposite the initial cut 825 as measured by imaging the biological tissue 800, a force between the blades 850 as measured using a strain sensor or other sensor of the retractor) and could responsively adjust a separation between the blades 850, a separating force applied between the blades 850, or perform some other operation of the retractor. For example, the robotic surgical system could operate an armature configured to control the position and/or orientation of the retractor to ensure that forces applied by the blades 850 to tissues opposite the initial cut 825 are substantially balanced. Additionally or alternatively, the robotic surgical system could indicate to a human a positioning of the retractor that could allow the robotic surgical system to operate the blades 850 of the retractor to apply a separating force between portions of biological tissue opposite the initial cut 825, and the human could position the retractor.

In some examples, the robotic surgical system could determine that a prospective surgical intervention (e.g., a cut into the biological tissue) could be dangerous (e.g., could cause a danger to health of a patient by causing blood loss, tissue trauma, nerve damage, or some other adverse health state). For example, the robotic surgical system could determine that a determined cut trajectory is within a specified distance of an obstacle or avoidance target. Responsive to such a determination, the robotic surgical system could indicate (e.g., using a user interface, using a control console of a tele-surgical system, using an augmented reality system) information about the obstacle, avoidance target, or other determined potentially dangerous condition and/or information related to such. For example, the robotic surgical system could indicate an image of the biological tissue with an overlay indicating the location of an obstacle or other element of the biological tissue and indicating the shape, location, or other information about a determined cut trajectory. The robotic surgical system could then receive some input from the user (e.g., modification information indicating one or more modifications of the cut trajectory, an instruction to perform a cut based on the indicated cut trajectory, or some other input). The robotic surgical system could then operate based on the received user input. Additionally or alternatively, the robotic surgical system could periodically (e.g., before each operation of a surgical instrument to cut into tissue) request input from a user (e.g., by indicating some information about a prospective cut or other operation of the robotic surgical system) and could operate responsive to the user input. Such operations of a robotic surgical system could be performed to increase the safety of operation of the robotic surgical system by including human oversight at regular intervals.

The robotic surgical system could be configured and/or operated to perform further surgical interventions. For example, where information indicative of a desired dissection includes a pre-surgical image of a biological tissue and a description of a target tissue within the biological tissue, the robotic surgical system or some other computational device could operate to determine, based on one or more images of the biological tissue, that the target tissue has been exposed by one or more dissections and/or cuts into the biological tissue performed by the robotic surgical system or by some other system or person. Responsive to such a determination, the robotic surgical system could operate to perform some other surgical intervention, e.g., operate a surgical instrument to resect, dissect, ablate, cauterize, or otherwise destroy the target tissue. Additionally or alternatively, the robotic surgical system could indicate that the target tissue has been exposed, and a surgeon could use the robotic surgical system (e.g., through a user interface, through a control console of a tele-surgical system), some other surgical system, or some other means to perform a surgical intervention on the target tissue (e.g., ablate the target tissue, ligate the target tissue, repair the target tissue, harvest the target tissue for transplant, place and/or install an implant).

A robotic surgical system as described herein could be configured and/or operated in additional ways. In some examples, the robotic surgical system could operate to record a variety of information relating to its effecting of a surgical intervention. Such information could include images of biological tissues, properties of the operation of the robotic surgical system to dissect the biological tissue (e.g., cut trajectories, information indicative of desired dissections, information describing the operation of retractors, imagers, surgical instruments, or other elements of the robotic surgical system), measured properties of the biological tissue (e.g., temperature, perfusion) and/or of a patient (e.g., blood pressure, heart rate, blood oxygenation), or other information. Such recorded information could be used to enable a variety of applications. For example, such information could be used to train human surgeons and/or to train or update algorithms used to operate the robotic surgical system. Such information could be used to predict outcomes of a surgical intervention (e.g., probability of infection, probability of wound dehiscence, probability of remission, probability of nerve or other damage) and/or to anticipate a course of post-operative care (e.g., doses of analgesics or other drugs, rehabilitative techniques, properties of chemotherapy or other cancer treatment regimens).

In some examples, such recorded information (e.g., recordings of the location, geometry, and other properties of dissected biological tissues before, during, and after dissection thereof) could be used to inform closing (i.e., suturing or otherwise restoring tissues dissected during a surgical intervention) of a wound or dissection created in the performance of a surgical intervention. For example, the robotic surgical system could present information to a surgeon (e.g., using an augmented reality display, using a display of a control console of a tele-surgical system) to allow the surgeon to approximate tissue or otherwise close a wound or dissection to minimize post-surgical recovery time or according to some other consideration. Additionally or alternatively, the robotic surgical system could operate one or more retractors to reverse previous operations of the one or more retractors to separate tissue (e.g., to reduce a displacement between blades of the one or more retractors) to allow for optimization of wound closure and/or tissue apposition (e.g., operating the one or more retractors such that tissues opposite a cut that were proximate before being cut are proximate after operation to remove the one or more retractors). Additional and alternative configurations and operations of a robotic surgical system are anticipated.

V. EXAMPLE ROBOTIC SURGICAL SYSTEM

Figure 9:
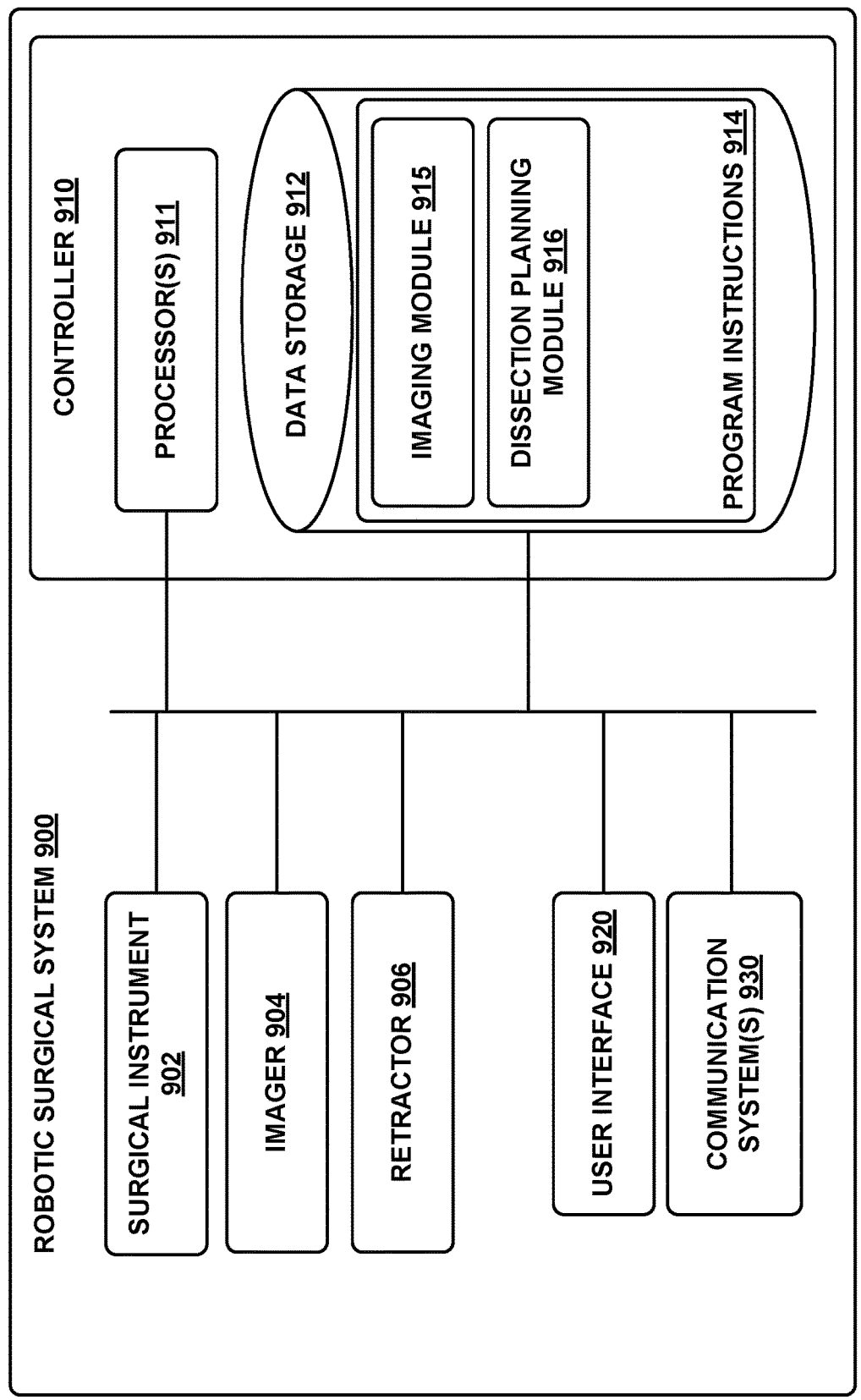
FIG. 9 is a functional block diagram of an example robotic surgical system.

FIG. 9 is a simplified block diagram illustrating the components of a robotic surgical system 900, according to an example embodiment. Robotic surgical system 900 may take the form of or be similar to the example robotic surgical system 100 shown in FIGS. 1A and 1B. Robotic surgical system 900 may take a variety of forms, such as a wall, surgical table, ceiling, or floor-mounted device. Robotic surgical system 900 could also take the form of a system, device, or combination of devices that is configured as part of another device, apparatus, or system. For example, Robotic surgical system 900 could take the form of a surgical instrument, imager, and other components configured to be mounted to or otherwise disposed as part of a surgical apparatus, tool, implement, or system (e.g., a stereotactic surgical apparatus, an imaging-guided surgical system). Robotic surgical system 900 could also take the form of a system configured to operate in some other industrial environment, medical environment, scientific environment, or some other environment. Robotic surgical system 900 also could take other forms.

In particular, FIG. 9 shows an example of a robotic surgical system 900 having a surgical instrument 902, an imager 904, a retractor 906, a user interface 920, communication system(s) 930 for transmitting data to and receiving data from a remote system, and controller 910. The components of the robotic surgical system 900 may be disposed on or within a mount or housing or on some other structure for mounting the system to enable stable imaging or other functions relative to elements in a surgical environment of interest, for example, to a surgical frame secured relative to a biological tissue subject to a surgical intervention.

Controller 910 may be provided as a computing device that includes one or more processors 911. The one or more processors 911 can be configured to execute computer-readable program instructions 914 that are stored in a computer readable data storage 912 and that are executable to provide the functionality of a robotic surgical system 900 as described herein.

The computer readable data storage 912 may include or take the form of one or more non-transitory, computer-readable storage media that can be read or accessed by at least one processor 911. The one or more computer-readable storage media can include volatile and/or non-volatile storage components, such as optical, magnetic, organic or other memory or disc storage, which can be integrated in whole or in part with at least one of the one or more processors 911.

In some embodiments, the computer readable data storage 912 can be implemented using a single physical device (e.g., one optical, magnetic, organic or other memory or disc storage unit), while in other embodiments, the computer readable data storage 912 can be implemented using two or more physical devices.

The surgical instrument 902 is configured to cut biological tissue, among other things (e.g., the surgical instrument 902 could additionally be configured to heat, ablate, cauterize, coagulate, or otherwise interact with and/or modify biological tissue). For example, the surgical instrument 902 could include a scalpel including one or more sharpened edges configured to cut tissue. Such a scalpel could be disposed on an armature configured to control the location and/or orientation of the scalpel such that the controller 910 could operate the armature to cut tissue using the scalpel according to some specified trajectory and/or desired dissection of the tissue. Additional or alternative cutting or other surgical instruments could be disposed on such an armature and operated to cut tissue according to an application. For example, a harmonic scalpel, an RF ablation probe, a thermal probe (e.g., a cryosurgical probe, a heat ablation probe), one or more electrodes of an electrosurgical and/or electrocautery system, or some other instrument could be disposed on such an armature and operated to cut tissue. The surgical instrument 902 could include a surgical laser, e.g., a 2 micron laser, $CO_2$ laser, an excimer laser, or some other variety of laser configured to apply energy to a specified portion of a biological tissue. One or more properties of such surgical instruments (e.g., an amplitude or frequency of vibration of a harmonic scalpel, a temperature or heat flux rate of a thermal probe, a wavelength or energy level of a beam illumination emitted by a surgical laser, a voltage, current, frequency, polarity, or other property of operation of an RF ablation probe or electrosurgical and/or electrocautery system) could be controlled to control one or more properties of the dissection of a tissue (e.g., a rate of ablation, an amount of tissue ablated, a rate of dissection, a depth of dissection, an amount of heat applied to tissues neighboring a dissection).

The imager 904 is configured to image a biological tissue and could be configured to generate images, three-dimensional data, scanning surfaces, or some other data about the geometry, structure, contents, or other properties of tissues. The imager 904 could include one or more cameras configured to receive light (e.g., visible light, infrared light, ultraviolet light) at one more wavelengths or ranges of wavelengths to generate one or more two-dimensional images of the tissue. The imager 904 could be configured to actively illuminate one or more portions of a biological tissue with light at one or more wavelengths. The imager 904 could be configured to determine the presence, location, concentration, or some other information about an analyte in tissue (e.g., about the presence and location of cancer cells and/or one or more analytes indicative of cancer cells). The imager 904 could be configured to determine three-dimensional information about the tissue, e.g., a three-dimensional description of the surface of the tissue, of boundaries or other features of or between tissues at the surface and/or within a biological tissue. The imager 904 could be configured to generate some volumetric information about the tissue (e.g., determining a density, water content, or some other information throughout a volume of tissue using, e.g., CT, MRI, OCT).

The retractor 906 includes two blades configured to separate two portions of tissue. The portions of tissue could be opposite a dissection of the tissue (such dissection produced by the robotic surgical system 900 or by some other means), a hiatus (e.g., cleft or other separation) between tissues, or related in some other way. The blades of the retractor could be smooth, have one or more sharp and/or blunt prongs configured to secure tissue, or configured in some other way to attach to and/or apply forces to portions of tissue. In some examples, blades of a retractor could apply suction or an adhesive to portions of tissue in order to apply separating forces to the portions of tissue. The retractor 906 could be disposed on an armature configured to control one or more properties of the location and/or orientation of the retractor. Alternatively, the retractor 906 could be self-retaining or otherwise configured to maintain position relative to a tissue without an armature or other securing means, and the retractor could be positioned by a surgeon (e.g., at a location indicated by the user interface 920). The blades of the retractor 906 could be actuated (e.g., by a motor or some other actuator) and a force, distance, rate of separation, or other properties of the separation of tissues by the retractor could be controlled by the controller 910.

The program instructions 914 stored on the computer readable data storage 912 may include instructions to perform any of the methods described herein. For instance, in the illustrated embodiment, program instructions 914 include an imaging module 915 and a dissection planning module 916.

The imaging module 915 can include instructions for operating the imager 902 to image a biological tissue and to determine one or more properties of the biological tissue based on such generated images. Generally, instructions in the imaging module 915 describe methods of operating the imager to receive light from portions of a biological tissue. Instructions of the imaging module 915 could additionally describe methods of operating the imager to illuminate portions of the biological tissue and to determine one or more properties (e.g., a shape, a fluorophore content, a location) of one or more tissues and/or regions of tissues within an images biological tissue. The imaging module 915 could additionally include instruction describing methods of determining a correspondence between two or more images of a biological tissue, e.g., between a pre-surgical image and an intra-surgical or other type of image of the biological tissue. Other operations, functions, and applications of the imager 902, and/or of other imaging components of a robotic surgical system as described herein could be implemented as program instructions in the imaging module 915.

The dissection planning module 916 can include instructions for determining a cut trajectory of the surgical instrument 902 to cut a biological tissue based on an image of the tissue (e.g., an image generated by the imager 902) and information indicative of a desired dissection of the biological tissue. The instructions of the dissection planning module 916 could include instructions to update information indicative of a desired dissection based on a determined correspondence between two or more images of the biological tissue. Instructions of the dissection planning module 916 could include instructions to determine that a determined cut trajectory is within a specified distance of an obstacle or could otherwise cause a negative health consequence to the biological tissue and/or to a patient containing the biological tissue. The instructions 916 could further include instructions to, responsive to such a determination, indicate information to a user, receive responsive input from the user, and plan a dissection or other operation based on the received input (e.g., implement the determined cut trajectory by controlling the surgical instrument accordingly, modify the determined cut trajectory and control the surgical instrument accordingly, pause the operation of the robotic surgical system 900). The instructions of the dissection planning module 916 could include instructions to determine that access to a particular portion of the biological tissue is restricted (e.g., that portions of biological tissue opposite a cut could be separated by the retractor 906) and to responsively operate the retractor 906 to apply a separating force between portions of the biological tissue to increase access to the particular portion of the biological tissue.

The dissection planning module 916 can include further instructions to operate armatures or other elements configured to control the location and/or orientation of elements (e.g., surgical instrument 902, imager 904, retractor 906, cameras, sources or suction, or other elements). Such instructions could include instructions to alter the location of the imager 902 or some other camera or imaging device to provide a view of a target tissue (e.g., the base of a cut). Such instructions could include instructions to alter the location of one or more elements of the robotic surgical system to match motion of one or more tissues undergoing a surgical intervention. Additionally or alternatively, armatures or other motion-control elements of a robotic surgical system could be wholly or partially controlled by one or more additional controllers or other processing elements of the armatures or other motion-control elements. Other operations, functions, and applications of the surgical instrument 902, retractor 906, and/or of other components of a robotic surgical system as described herein could be implemented as program instructions in the dissection planning module 916.

Some of the program instructions of the imaging module 915 and/or dissection planning module 916 may, in some examples, be stored in a computer-readable medium and executed by a processor located external to the robotic surgical system 900. For example, the robotic surgical system 900 could be configured to image a portion of a biological environment and then transmit related data to a remote server, which may include a mobile device, a personal computer, the cloud, or any other remote system, for further processing (e.g., for the determination of one or more prospective cut trajectories, updated information indicative of a desired dissection, or other information related to the control of the robotic surgical system 900 to effect a surgical intervention). Resulting information related to the operation of the robotic surgical system 900 could then be received from the remote system and used to operate the surgical instrument 902, imager 904, and/or retractor 906.

User interface 920 could include indicators, displays, buttons, touchscreens, head-mounted displays, augmented reality devices, displays of a console of a tele-surgical system, and/or other elements configured to present information about the robotic surgical system 900 to a user and/or to allow the user to operate the robotic surgical system 900. Additionally or alternatively, the robotic surgical system 900 could be configured to communicate with another system (e.g., a cell phone, a tablet, a computer, a remote server) and to present elements of a user interface using the remote system. The user interface 920 could be disposed proximate to the surgical instrument 902, imager 904, retractor 906, controller 910, or other elements of the robotic surgical system 900 or could be disposed away from other elements of the robotic surgical system 900 and could further be in wired or wireless communication with the other elements of the robotic surgical system 900. The user interface 920 could be configured to allow a user to specify some operation, function, desired dissection, modification of a cut trajectory, or property of operation of the robotic surgical system 900. The user interface 920 could be configured to present information about a biological tissue, prospective surgical intervention, or other contents of a surgical environment (e.g., a tissue type, a presence of fluorophore) to the user using a display, to present a degree of progress of an ongoing function of the robotic surgical system (e.g., a degree of progress in dissecting a biological tissue along a desired trajectory using the surgical instrument 902), to present an image of a biological tissue or other contents of the surgical environment generated using the imager 904, or using some other imaging component or sensor, or to present some other information to a user. Other configurations and methods of operation of a user interface 920 are anticipated.

Communication system(s) 930 may also be operated by instructions within the program instructions 914, such as instructions for sending and/or receiving information via a wireless antenna, which may be disposed on or in the robotic surgical system 900. The communication system(s) 930 can optionally include one or more oscillators, mixers, frequency injectors, etc. to modulate and/or demodulate information on a carrier frequency to be transmitted and/or received by the antenna. In some examples, the robotic surgical system 900 is configured to indicate an output from the controller 910 by transmitting an electromagnetic or other wireless signal according to one or more wireless communications standards (e.g., Bluetooth, WiFi, IRdA, ZigBee, WiMAX, LTE). In some examples, the communication system(s) 930 could include one or more wired communications interfaces and robotic surgical system 900 could be configured to indicate an output from the controller 910 by operating the one or more wired communications interfaces according to one or more wired communications standards (e.g., USB, FireWire, Ethernet, RS-232).

The computer readable data storage 912 may further contain other data or information, such as medical and health history of a patient whose biological tissue is being imaged or otherwise interacted with by the robotic surgical system 900, that may be useful in imaging, dissecting, ablating, retracting, or otherwise interacting with a biological tissue or other environment of interest. Further, the computer readable data storage 912 may contain data corresponding to imaging information about a biological tissue or other environment of interest. The computer readable data storage 912 may contain calibration data corresponding to a configuration of the robotic surgical system 900 or some other information. Calibration, model, imaging, and/or other data may also be generated by a remote server and transmitted to the robotic surgical system 900 via communication system(s) 930.

In some examples, the collected calibration and/or model data, stored information about operation of the robotic surgical system 900 (e.g., recorded information about a surgical intervention performed by the robotic surgical system 900), health state information (e.g., health state of biological tissues) detected by the robotic surgical system 900 and other usage or other information may additionally be input to a cloud network (e.g., using the communications system(s) 930) and be made available for download by users having sufficient permissions (e.g., a surgeon tasked with reviewing the outcome of a surgical intervention wholly or partially effected using the robotic surgical system 900). Other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring outcomes of a surgical intervention or other treatment. For example, high-density, real-time data may be collected from a population of device users who have experienced a surgical intervention implemented using information generated by the robotic surgical system 900 to assess the safety and efficacy of the surgical intervention. Such data may also be used on an individual level to assess a particular patient's response to a surgical intervention or therapy. Based on this data, a physician or clinician may be able to tailor a future surgical intervention or other treatment to suit an individual's needs.

VI. EXAMPLE METHODS

Figure 10:
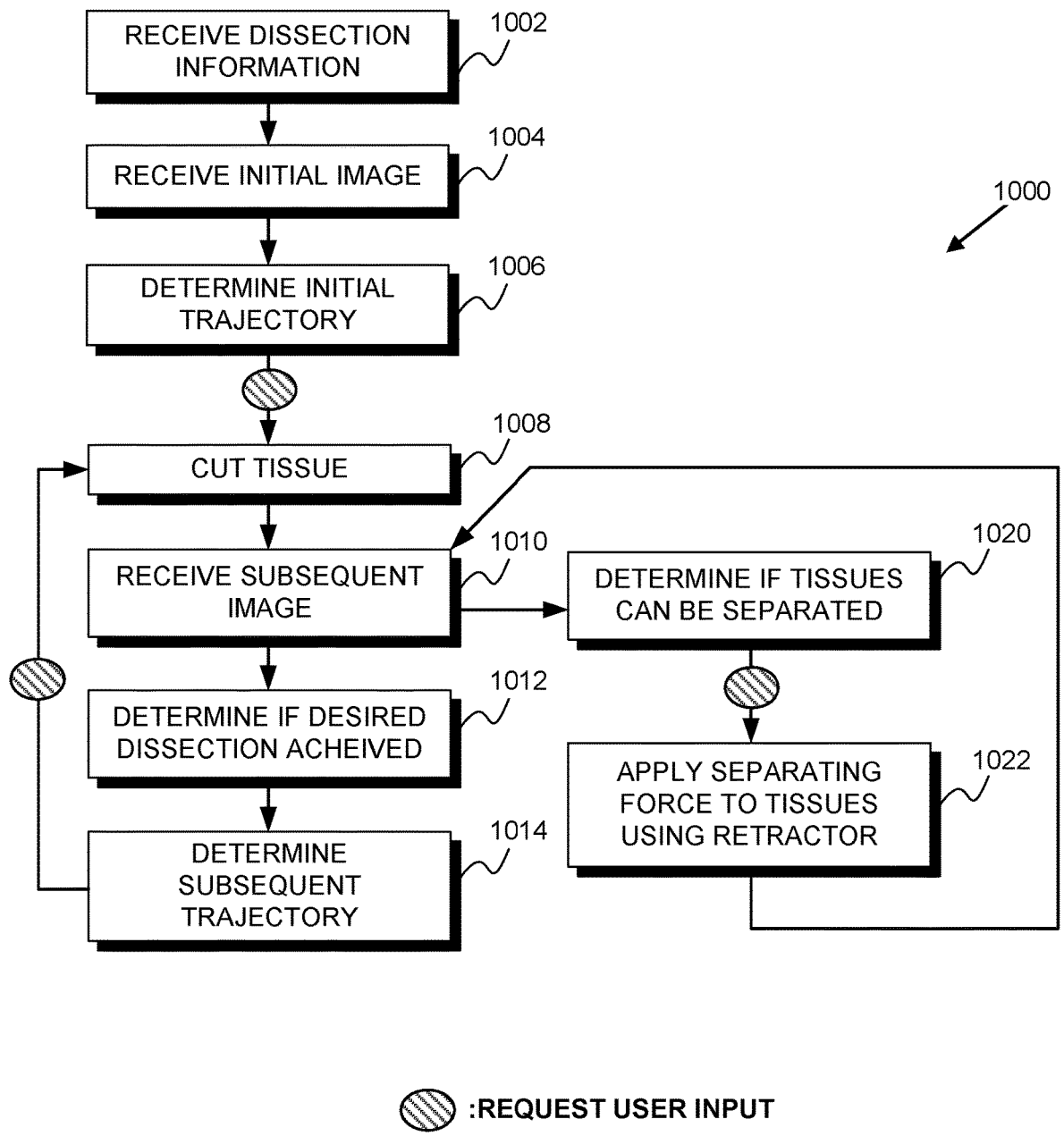
FIG. 10 is a flowchart of an example method.

FIG. 10 is a flowchart of a method 1000 for operating elements of a robotic surgical system to perform functions and/or applications of the robotic surgical system. The robotic surgical system includes a surgical instrument configured to cut biological tissue (e.g., a scalpel, a surgical laser, an RF or electrical cautery or ablation tool). The robotic surgical system further includes a retractor configured to apply a separating force between two or more portions of the biological tissue. The robotic surgical system additionally includes a controller configured to control the surgical instrument and the retractor and to perform the elements of the method.

The method 1000 includes receiving dissection information (1002). This could include receiving information indicative of a desired dissection of the biological tissue from a remote system (e.g., from a server, from a control console of a tele-surgical system), from a user interface of the robotic surgical system (e.g., a control touchscreen, an augmented reality device worn by a surgeon, a gesture detection interface), or from some other system(s). A desired dissection could be indicated by information describing a particular surface in space, defined relative to an element of the robotic surgical system and/or a feature of the biological tissue. For example, a desired dissection could be described by information specifying a surgical plane or other boundary between specified tissues and/or specified regions of tissues. A desired dissection could be described by a location relative to a tissue to dissect into and/or a direction in which to dissect. Information describing a dissection could include information describing a target to fully or partially expose (e.g., a tumor located beneath an overlying tissue, a blood vessel, nerve, or other tissue to be repaired, ligated, or otherwise manipulated that is location beneath an overlying tissue). Information describing a dissection could also describe the location, shape, extent, or other information about tissues and/or regions of tissue not to dissect, e.g., nerves, blood vessels, ducts, tendons, important regions of cortex, or some other specified regions of tissue.

The method 1000 additionally includes receiving an initial image of the biological tissue (1004). This could include operating an imager (e.g., a camera, a 3-D scanner, a fluorescent imager, a spectroscope, a hyperspectral imager) of the robotic surgical system. Receiving an initial image of the biological tissue (1004) could include receiving imaging data from an imaging device that is not a part of the robotic imaging system (e.g., a CT scanner, an MR imager). Receiving an initial image of the biological tissue (1004) could include illuminating the biological tissue with light at a wavelength corresponding to an excitation wavelength of a fluorophore that is present in the biological tissue and detecting light at a wavelength corresponding to an emission wavelength of the fluorophore.

The method 1000 additionally includes determining an initial trajectory (1006). This could include determining, based on the initial image and received information indicative of a desired dissection, an initial trajectory of the surgical instrument to cut the biological tissue. The initial trajectory could be specified not to achieve the complete desired dissection; that is, the initial trajectory could specify a short and/or shallow cut, such that any changes in the biological tissue (e.g., deformation or translation of the tissue due to external forces, the action of the robotic surgical system) could be compensated for by receiving a subsequent image (1010), and generating a related, 'updated' subsequent trajectory (1014) before the development of a significant deviation between an initial image of the tissue (and an initial trajectory developed therefrom) and the state of the actual biological tissue. In some examples, determining an initial trajectory could include determining whether a determined initial trajectory is within a specified distance of an avoidance target (i.e., a region of tissue specified by information indicative of a desired dissection as not to be dissected) and/or some other obstacle (e.g., a nerve, blood vessel, or other tissue feature detected in the initial image) and updating the determined initial trajectory to avoid the avoidance target and/or obstacle. In some examples, determining an initial trajectory (1006) could include updating a description of a desired dissection, a target tissue, an avoidance tissue, or some other specified contents of a biological tissue based on a correspondence between the initial image and some previous image of the biological tissue (e.g., a pre-surgical image).

The method 1000 additionally includes cutting the biological tissue (1008). This could include controlling the surgical instrument, based on the initial trajectory, such that the surgical instrument makes an initial cut into the biological tissue. Cutting the biological tissue (1008) could include controlling the surgical instrument, based on a subsequent trajectory, such that the surgical instrument makes a subsequent cut into the biological tissue. Cutting the biological tissue (1008) could include the robotic surgical system receiving a plurality of images of the biological tissue over time (e.g., at a high frequency, e.g., 10s to 100s of Hertz), responsively updating the initial trajectory and/or subsequent trajectories in response to one or more of the plurality of images, and controlling the surgical instrument to make the initial cut according to the updated initial trajectory and/or subsequent trajectories. In some examples, this could include increasing/decreasing a power of a beam of light emitted by a surgical laser, increasing/decreasing a force applied to a scalpel by an armature, increasing/decreasing a voltage and/or current applied to a probe or electrode, or some other change of one or more controlled properties of operation of a surgical instrument such that a depth of the cut is substantially equal to a depth of cut specified by the initial trajectory.

The method 1000 additionally includes receiving a subsequent image of the biological tissue (1010). This could include, after the surgical instrument has made an initial and/or subsequent cut into the biological tissue, receiving a subsequent image of the biological tissue that shows the initial and/or subsequent cut(s) and at least a portion of biological tissue surrounding the initial and/or subsequent cut(s). This could include operating an imager (e.g., a camera, a 3-D scanner, a fluorescent imager, a spectroscope, a hyperspectral imager) of the robotic surgical system. Receiving subsequent image of the biological tissue (1010) could include receiving imaging data from an imaging device that is not a part of the robotic imaging system (e.g., a CT scanner, an MR imager). Receiving a subsequent image of the biological tissue (1010) could include illuminating the biological tissue with light at a wavelength corresponding to an excitation wavelength of a fluorophore that is present in the biological tissue and detecting light at a wavelength corresponding to an emission wavelength of the fluorophore.

The method 1000 additionally includes determining if a desired dissection of the biological tissue has been achieved (1012). This could include determining, based on the subsequent image and information indicative of the desired dissection, whether the initial cut has achieved the desired dissection. For example, the robotic surgical system could determine whether any tissue still existed along a desired dissection surface describe in the information indicative of the desired dissection.

The method 1000 additionally includes determining a subsequent trajectory (1014). This could include determining, based on the subsequent image and received information indicative of a desired dissection, one or more subsequent trajectories of the surgical instrument to cut the biological tissue.

A subsequent trajectory could be specified not to achieve the complete desired dissection; that is, the subsequent trajectory could specify a short and/or shallow cut, such that any changes in the biological tissue (e.g., deformation or translation of the tissue due to external forces, the action of the robotic surgical system) could be compensated for by: receiving a further subsequent image (1010), and generating a related, 'updated' further subsequent trajectory (1014) before the development of a significant deviation between the preceding subsequent image of the tissue (and a preceding subsequent trajectory developed therefrom) and the state of the actual biological tissue. In some examples, determining a subsequent trajectory could include determining whether a determined subsequent trajectory is within a specified distance of an avoidance target (i.e., a region of tissue specified by information indicative of a desired dissection as not to be dissected) and/or some other obstacle (e.g., a nerve, blood vessel, or other tissue feature detected in the initial image) and updating the determined subsequent trajectory to avoid the avoidance target and/or obstacle. In some examples, determining a subsequent trajectory (1006) could include updating a description of a desired dissection, a target tissue, an avoidance tissue, or some other specified contents of a biological tissue based on a correspondence between the subsequent image and some previous image of the biological tissue (e.g., a pre-surgical image, an initial image, a preceding subsequent image).

The method 1000 additionally includes determining if tissues of the biological tissue can be separated (1020). This could include determining, based on the subsequent image and information indicative of the desired dissection, whether two portions of biological tissue opposite the initial and/or subsequent cut(s) can be separated by the retractor to improve access of the surgical instrument to the biological tissue at the base of the initial and/or subsequent cut(s). For example, the robotic surgical system could determine, based on one or more images of the biological tissue, that the base of a cut in the tissue is wholly or partially occluded, is at the base of a cut having a high aspect ratio (i.e., a large depth compared to its width), or some other determination related to accessing and/or imaging tissue at the base of the cut. Other operations of the robotic surgical system to perform this determination are anticipated.

The method 1000 additionally includes applying separating forces to tissues of the biological tissue using the retractor (1022). This could include, responsive to determining that the two portions of biological tissue opposite the initial and/or subsequent cut(s) can be separated by the retractor to improve access of the surgical instrument to the biological tissue at the base of the initial cut, controlling an armature to position the retractor between the two portions of biological tissue opposite the initial and/or subsequent cut(s) and controlling the retractor to apply a separating force between the two portions of biological tissue opposite the initial and/or subsequent cut(s). For example, the robotic surgical system could translate and/or rotate the retractor (e.g., using an armature configured for such) to position blades of the retractor within a cut in the tissue. The retractor could then be operated by the robotic surgical system to apply a separating force between two or more portions of tissue opposite the cut to separate the two or more portions of tissue and to provide access to tissue locations (e.g., tissue at the base of the cut) deep relative to the two or more portions of tissue.

Transitions (i.e., arrows) between steps of FIG. 10 having a hatched circle indicator (labeled in FIG. 10 as indicating a request for user input) indicate that a robotic surgical system could, before performing a step subsequent to such a transition, make some sort of request for user (e.g., a surgeon) input and/or indicate some information to a user. For example, the robotic surgical system could determine that a determined prospective operation of the robotic surgical system (e.g., a cut of the tissue, a retraction of the tissue) could have a negative health consequence for the biological tissue and/or a person containing the biological tissue. Responsive to such a determination, the robotic surgical system could indicate (e.g., using a user interface, using a control console of a tele-surgical system, using an augmented reality system) information about the prospective operation and/or information related to such. The robotic surgical system could then receive some input from the user (e.g., modification information indicating one or more modifications to a prospective operation, an instruction permitting performance of the prospective operation, or some other input). The robotic surgical system could then operate based on the received user input. Note that the location of the hatched circles over particular transitions (i.e., arrows) within FIG. 10 is meant as a non-limiting example. Fewer or more of the illustrated transitions, or transitions between illustrated steps and additional steps of the method 100 (not shown), could include indication of information to a user and/or requests for user interaction/input.

In another example, the robotic surgical system could, before each transition indicated by the hatched circle, request input from the user (e.g., by indicating some information about a prospective cut or other operation of the robotic surgical system) and could operate responsive to the user input. Such operations of a robotic surgical system could be performed to increase the safety of operation of the robotic surgical system by including human oversight at regular intervals and/or before any operation of the robotic surgical system to ablate, retract, heat, dissect, or otherwise manipulate the biological tissue.

The method 1000 could include additional steps. For example, the method could include operating the robotic surgical system to perform some additional surgical intervention once a desired dissection has been achieved, e.g., ablating a target (e.g., a tumor) that has been exposed by achieving the desired dissection. Additional operations of a robotic surgical system, and alternative implementations of operations of a robotic surgical system as described herein, are anticipated.

The method 1000 could include other additional steps or elements. The method 1000 could include any additional steps, or could include details of implementation of the listed steps 1002, 1004, 1006, 1008, 1010, 1012, 1014, 1020, 1022 or of other additional steps, as described herein in relation to the operation of a robotic surgical system. Additional and alternative steps of the method 1000 are anticipated.

In some examples, the biological tissue(s) described in relation to the method 1000 above could be biological tissue(s) of a human body. For example, the biological tissue(s) could have been determined to include a tumor that could be resected, ablated, or otherwise removed to change and/or affect a health state of the human body. Other examples of surgical environments, biological tissues, surgical interventions, surgical instruments, methods of operating a robotic surgical system, configurations of robotic surgical systems, and other elements are anticipated.

VII. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, information about a surgical intervention performed on the user, information about biological tissues of a user, a user's preferences, or a user's current location), or to control whether and/or how to receive content from a content server (e.g., a profile of power to ablate a tissue applied using a surgical laser) that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a hospital, city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to image and/or manipulate biological environments (e.g., tissues) of a human body, it is noted that the disclosed devices, systems, and methods can be applied in other contexts as well. For example, imaging, cutting, and/or retraction systems configured as disclosed herein may be included as part of other surgical and/or medical imaging apparatus. In some contexts, such a robotic surgical system could be operated to detect one or more properties of a tissue or other element of a human body, possibly in concert with other medical imaging or other sensor apparatus. In another example, a robotic surgical system could be configured to image, ablate, cut, resect, retract, suture, and/or perform some other interaction or surgical intervention on specified elements and/or regions of a non-tissue element of a human body. For example, the robotic surgical system could be configured and/or applied to image, cut, heat, or otherwise manipulate specified regions of an implantable device (e.g., a stent, an artificial joint, a pacemaker) to control the effecting of a desired change in the implantable device (e.g., to section the device, to weld an element of the device, to activate an element of the device, to trim an element (e.g., an electrode) of the device).

In other examples, devices, systems, and methods disclosed herein may be applied to image and/or manipulate regions of environments that are not in or on a human body. For example, robotic surgical systems disclosed herein may be included in systems used to image and/or manipulate specified regions (e.g., tissues) of an animal. In another example, devices, systems, and methods disclosed herein may be applied to image and/or manipulate regions of an industrial environment or a work element of an industrial process, such as a work element in a textile manufacturing process, plant matter, food, or other materials in a food processing process, or as a part of an industrial and/or municipal waste handling process.

Additionally, while various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A method comprising:
receiving, by a controller, information indicative of a desired dissection of a biological tissue, wherein the controller is configured to control a surgical instrument and a retractor, wherein the surgical instrument is configured to cut the biological tissue;
receiving, by the controller, an initial image of the biological tissue;
determining, by the controller, based on the initial image and the information indicative of the desired dissection, an initial trajectory of the surgical instrument to cut the biological tissue;
controlling, by the controller, the surgical instrument based on the initial trajectory, such that the surgical instrument makes an initial cut into the biological tissue;
after the surgical instrument has made the initial cut into the biological tissue, receiving, by the controller, a subsequent image of the biological tissue, wherein the subsequent image shows the initial cut and at least a portion of the biological tissue surrounding the initial cut;

determining, by the controller, based on the subsequent image and the information indicative of the desired dissection, whether two portions of biological tissue opposite the initial cut can be separated by the retractor; and responsive to determining that the two portions of biological tissue opposite the initial cut can be separated by the retractor, the controller (i) positioning the retractor between the two portions of biological tissue opposite the initial cut, and (ii) controlling the retractor to apply a separating force between the two portions of biological tissue opposite the initial cut.

2. The method of claim 1, wherein the information indicative of a desired dissection of the biological tissue comprises a pre-surgical image of the biological tissue and a description of the desired dissection defined relative to the pre-surgical image, and wherein determining, by the controller, based on the initial image and the information indicative of the desired dissection, an initial trajectory of the surgical instrument to cut the biological tissue comprises:

updating the description of the desired dissection based on a correspondence between the pre-surgical image and the initial image of the biological tissue; and determining the initial trajectory of the surgical instrument to cut the biological tissue based on the updated description of the desired dissection.

3. The method of claim 2, wherein the information indicative of a desired dissection of the biological tissue further comprises a description of an avoidance target defined relative to the pre-surgical image, and wherein determining, by the controller, based on the initial image and the information indicative of the desired dissection, an initial trajectory of the surgical instrument to cut the biological tissue further comprises:

updating the description of the avoidance target based on a correspondence between the pre-surgical image and the initial image of the biological tissue;

determining whether the updated description of the avoidance target is within a specified distance of the determined initial trajectory of the desired dissection; and responsive to determining whether the updated description of the avoidance target is within a specified distance of the determined initial trajectory of the desired dissection, updating the determined initial trajectory of the desired dissection to avoid the updated description of the avoidance target.

4. The method of claim 2, wherein the description of the desired dissection is coincident with a surgical plane between regions of tissue.

5. The method of claim 2, wherein the information indicative of a desired dissection of the biological tissue further comprises a description of a target tissue, wherein achieving the desired dissection comprises exposing the target tissue, and wherein the method further comprises:

determining, by the controller, based on the subsequent image and the information indicative of the desired dissection, whether the target tissue is exposed; and responsive to determining that the target tissue is exposed, the controller controlling a surgical instrument to ablate the target tissue.

6. The method of claim 1, wherein controlling the retractor to apply the separating force between the two portions of biological tissue comprises controlling at least one of a magnitude of the separating force or a displacement between the two portion of biological tissue.

7. The method of claim 1, wherein the method further comprises:

determining, by the controller, based on the initial image the location of an obstacle in the biological tissue;

determining whether the location of the obstacle is within a specified distance of the determined initial trajectory of the desired dissection; and responsive to determining whether the location of the obstacle is within a specified distance of the determined initial trajectory of the desired dissection, updating the determined initial trajectory of the desired dissection to avoid the location of the obstacle.

8. The method of claim 1, wherein the method further comprises:

determining, by the controller, based on the initial image the location of an obstacle in the biological tissue;

determining whether the location of the obstacle is within a specified distance of the determined initial trajectory of the desired dissection; and responsive to determining whether the location of the obstacle is within a specified distance of the determined initial trajectory of the desired dissection:

indicating information about the obstacle, the initial trajectory of the desired dissection, and the initial image using a display;

receiving trajectory modification information; and updating the initial trajectory of the desired dissection based on the trajectory modification information.

9. The method of claim 1, wherein the initial image and the subsequent image of the biological tissue are received from a camera, wherein the camera is disposed on an armature that is configured to control the location and the orientation of the camera, and further comprising:

determining, by the controller, whether the subsequent image shows the biological tissue on both sides of the initial cut; and responsive to determining that subsequent image does not show the biological tissue on both sides of the initial cut, the controller controlling the armature to position the camera to provide a view of the biological tissue on both sides of the initial cut.

10. The method of claim 1, wherein the surgical instrument comprises at least one of: a surgical laser, scalpel, or electrocauterizer.

11. The method of claim 1, wherein the initial image and the subsequent image of the biological tissue are received from an imager, wherein the controller is configured to control the imager, and wherein receiving an image of the biological tissue from the imager comprises:

emitting, from the imager, light at an excitation wavelength of a fluorophore;

detecting, using the imager, light at an emission wavelength of the fluorophore; and generating, by the controller, an image of the fluorophore in the biological tissue based on the light at the emission wavelength detected using the imager.

12. The method of claim 1, further comprising:

determining, by the controller, based on the subsequent image and the information indicative of the desired dissection, whether the initial cut has achieved the desired dissection; and responsive to determining that the initial cut has not achieved the desired dissection, the controller (i) determining one or more subsequent trajectories of the surgical instrument to cut into the biological tissue, and (ii) controlling the surgical instrument based on the one or more subsequent trajectories, such that the surgical instrument makes one or more subsequent cuts into the biological tissue.

* * * * *